(12) United States Patent
Durgin et al.

(10) Patent No.: US 6,849,078 B2
(45) Date of Patent: *Feb. 1, 2005

(54) APPARATUS AND METHOD FOR COMPRESSING BODY TISSUE

(75) Inventors: Russell F. Durgin, Attleboro, MA (US); Marc O. Schurr, Tuebingen (DE); Gerhard Buess, Tuebingen (DE); Bernd Vogel, Karlsruhe (DE); Harald Fischer, Karlsruhe (DE)

(73) Assignee: Ovesco Endoscopy, GmbH, Tubingen (DE)

( * ) Notice: Subject to any disclaimer, the term of this patent is extended or adjusted under 35 U.S.C. 154(b) by 358 days.

This patent is subject to a terminal disclaimer.

(21) Appl. No.: 09/956,902

(22) Filed: Sep. 21, 2001

(65) Prior Publication Data

US 2002/0032454 A1 Mar. 14, 2002

Related U.S. Application Data

(63) Continuation of application No. 09/443,219, filed on Nov. 18, 1999, now Pat. No. 6,428,548.

(51) Int. Cl.$^7$ .............................................. A61B 17/04
(52) U.S. Cl. ........................ 606/142; 606/151; 606/157
(58) Field of Search ................................ 606/151, 142

(56) References Cited

U.S. PATENT DOCUMENTS

| | | | | |
|---|---|---|---|---|
| 5,976,159 A | * | 11/1999 | Bolduc et al. | ............... 606/142 |
| 6,171,321 B1 | * | 1/2001 | Bolduc et al. | ............... 606/153 |
| 6,183,446 B1 | * | 2/2001 | Show et al. | ................ 606/151 |

* cited by examiner

Primary Examiner—Gary Jackson
(74) Attorney, Agent, or Firm—William W. Jones

(57) ABSTRACT

A system and method for delivering a surgical clip to a surgical site within a patient's body to compress body tissue is disclosed. In one embodiment for the system of the present invention, the system includes an endoscopic device that has an endoscope cap disposed on a distal end of the endoscopic device. A surgical clip is removably disposed on an outside surface of the endoscope cap. A deployment device is associated with the surgical clip for deploying the surgical clip from the endoscope cap to the body tissue that is to be compressed.

66 Claims, 31 Drawing Sheets

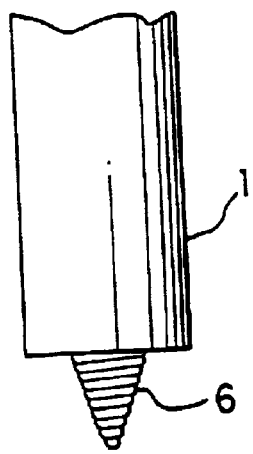
FIG.11    FIG.12
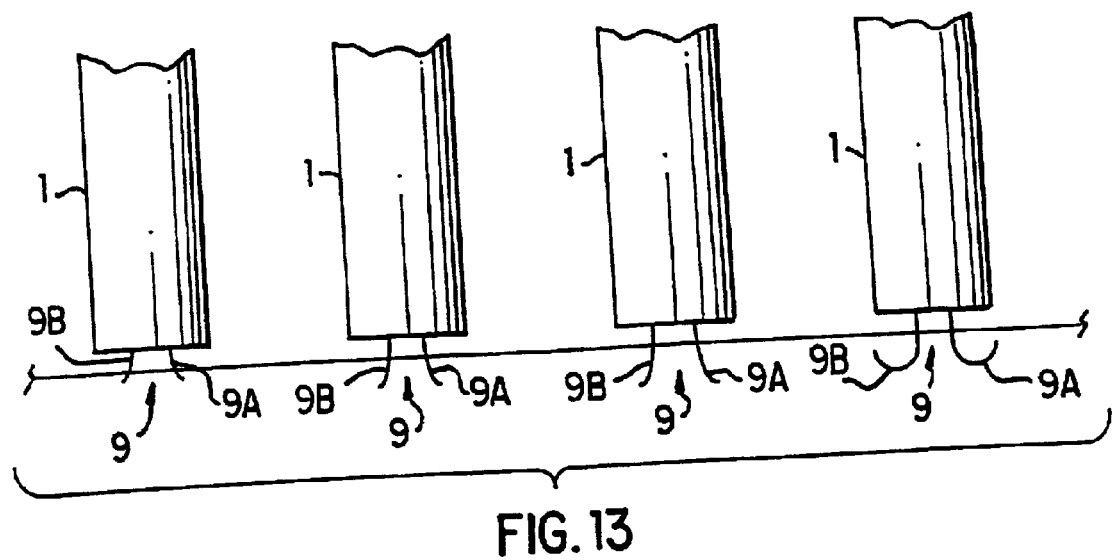
FIG.13

APPARATUS AND METHOD FOR COMPRESSING BODY TISSUE

RELATED APPLICATIONS

This is a Continuation of U.S. Ser. No. 09/443,219, filed on Nov. 18, 1999, now U.S. Pat. No. 6,428,548 title Apparatus and Method for Compressing Body Tissue.

BACKGROUND OF THE INVENTION

1. Field of the Invention

The present invention relates generally to an apparatus and method for compressing body tissue to prevent hemorrhaging at a surgical site within a patient's body. More specifically, the invention provides a clip and a system for delivering the clip to the surgical site. The present invention could be utilized for any of a variety of procedures, including to close an organ perforation from inside a lumen by approximating and compressing the wound edges of the perforated tissue.

2. Description of the Related Art

Bleeding Peptic Ulcer Disease can be a critical event since there is internal hemorrhaging associated with the ulcer. Patients that are suspected of having bleeding peptic ulcer disease can be diagnosed and treated endoscopically in emergency rooms of medical centers, intensive care units, or, in a Gastro-Intestinal (GI) suite, although personnel and equipment may need to be transported to the patient. Surgery, either laparoscopic or open, is an option. For example, if the diseased tissue is beyond repair, a surgical gastric resection may have to be performed. However, surgery is not preferred unless there is no endoscopic alternative or if previous endoscopic efforts have not succeeded. Surgical intervention is not preferred for at least the reasons that it has associated with it greater morbidity and mortality, and also, significantly higher costs than other procedures.

Ulcers are classified from clean ulcer to active spurting bleeding. The most worrisome are active bleeders and visible vessels. Untreated visible vessels are likely to bleed. For the GI endoscopist, hemorrhaging is the most worrisome procedure. It is his/her only unplanned, emergency procedure where time is critical in determining the success or failure of the procedure. It is the one problem the endoscopist faces that is generally not an outpatient procedure.

The endoscopist generally has a primary success rate of about 90% in treating bleeding ulcers; the balance are usually referred to surgery. All identified ulcers may re-bleed at a later time, whether endoscopically treated or untreated, but the re-bleed rate for endoscopically treated active bleeds and visible vessels is generally 10–30%. These rates have not improved significantly in decades.

The long-term probability of success of surgery in treating a bleeding ulcer, i.e., no re-bleed of the ulcer or permanent hemostasis, is virtually 100%. The reason that surgery has a higher success rate is because the bleeding site is compressed mechanically. Using either sutures or staples, the bleeding vessel is ligated, or tissue around the bleed site is compressed, ligating all of the surrounding vessels.

At present, the endoscopist has two widely used, and some lesser used (or experimental) therapeutic modalities for hemostasis. The most widely used are thermal and injection therapy. Some of the lesser used options are a mechanical clip, a loop, lasers and argon plasma cautery. However, drawbacks exist with these known procedures for the endoscopist. A brief description of these procedures are provided below.

In thermal therapy, a catheter with a rigid, heating element tip is passed through a working channel of an endoscope after the bleed is visualized and diagnosed. After the rigid catheter tip has exited the endoscope, the endoscope is manipulated to press the tip against the bleed site. Thermal power is then applied which desiccates and cauterizes the tissue. The combination of the tip compressing the tissue/vessel during thermal application essentially (theoretically) welds the vessel closed. Thermal generation is accomplished by either a resistive element within the tip or by applying RF energy through the tissue. However, both methods require a specialized power generator.

For injection therapy, a catheter with a distally extendible hypo-needle is passed through a working channel of an endoscope after the bleed is visualized and diagnosed. After the catheter tip has exited the endoscope, the endoscope is manipulated to the bleed site, the needle is extended remotely and inserted into the bleed site. A "vasoconstricting", liquefied drug is remotely injected through the needle. The drug constricts the vessels to stop the bleeding. The most common drug is saline diluted epinephrine; alcohol is another option. This procedure usually requires that multiple injections be performed in, and peripherally around, the bleeding site until hemostasis is observed.

Of the above two modalities, the preferred modality is dependent, generally, upon the geographic region in which it is performed. Different modalities are preferred in different geographic regions. In some areas and institutions, both therapies are combined in an attempt to improve the outcome of the procedure.

For mechanical compression, loops and mechanical clips are known for use, however, problems exist with each. A known loop is a snare-like loop that is passed through an endoscope's working channel via a flexible delivery catheter. The loop is placed around the bleeding site and retracted into the delivery catheter similar to the closing of a snare. The loop has a sliding member with a friction interface against the loop that acts like a draw string lock. After the loop is closed and locked around the site, the assembly is unattached from the delivery catheter. Whereas the loop is an endoscopically delivered compression devices its primary use is for bleeding polyp stalks, and thus, it is not designed for, nor appropriate for use in, ulcer treatment procedures.

A mechanical clip is known, however, the known mechanical clip has drawbacks. The known clip is a two legged clip that is passed through an endoscope's working channel via a flexible delivery catheter. The jaws of the clip are remotely opened, pushed into the bleeding site, closed and detached. Because of the requirement to pass the clip through the endoscope, the clip's size must be limited which prevents the clip from being able to clamp off all of the vessels in the tissue around the wound. Additionally, the clip is not able to provide sufficient clamping force because of its structural design. Thus, these clips require multiple applications and are not effective for definitive hemostasis. An additional problem with these clips is that when delivering these clips to the wound site, good visualization of the bleeding vessel cannot be obtained. The endoscopist may be required to blindly attach the clip, resulting in an imprecisely preformed procedure that may require guess work on the part of the endoscopist.

Therefore, it would be desirable to provide an improved system and method for endoscopically treating bleeding ulcers which could bring the initial hemostasis success rate for the endoscopic procedure in-line with the success rate achievable in surgical procedures. This system and method would provide for an improved capability to mechanically compress the bleeding site to achieve an effect which is commensurate with that obtainable in a surgical procedure.

SUMMARY OF THE INVENTION

A system and method for delivering a surgical clip to a surgical site within a patient's body to compress body tissue is provided. In one embodiment for the system of the present invention, the system includes an endoscopic device that has an endoscope cap disposed on a distal end of the endoscopic device. A surgical clip is removably disposed on an outside surface of the endoscope cap. A deployment device is associated with the surgical clip for deploying the surgical clip from the endoscope cap to the body tissue that is to be compressed.

In an embodiment for the method of the present invention, the method includes the steps of disposing a surgical clip on the outside surface of the endoscope cap where the endoscope cap is disposed on the distal end of an endoscopic device. The endoscopic device is deployed to the site within the patient's body such that the surgical clip is positioned proximate to the body tissue that is to be compressed. The body tissue is drawn within the endoscope cap and the surgical clip is deployed from the outside surface of the endoscope cap.

In an embodiment for a surgical clip in accordance with the present invention, the clip includes a first elongated tissue grasping surface having a first end and a second end and a second elongated tissue grasping surface having a first end and a second end. A first joint is connected at a first end to the first end of the first tissue grasping surface and is connected at a second end to the first end of the second tissue grasping surface. A second joint is connected at a first end to the second end of the first tissue grasping surface and is connected at a second end to the second end of the second tissue grasping surface. The first grasping portion and the second grasping portion are movable between a tissue receiving position and a tissue grasping position. When the first and second grasping portions are in the tissue receiving position, the first and second grasping portions are adapted to be received on the outer surface of the endoscopic device.

BRIEF DESCRIPTION OF THE DRAWINGS

The various features of the invention will best be appreciated by simultaneous reference to the description which follows and the accompanying drawings, in which:

FIG. 11 illustrates a first embodiment for a tissue grasping device in accordance with the principles of the present invention;

FIG. 12 illustrates a second embodiment for a tissue grasping device;

FIG. 13 illustrates a third embodiment for a tissue grasping device as it is sequentially inserted into an organ wall;

DETAILED DESCRIPTION

Figure 1:
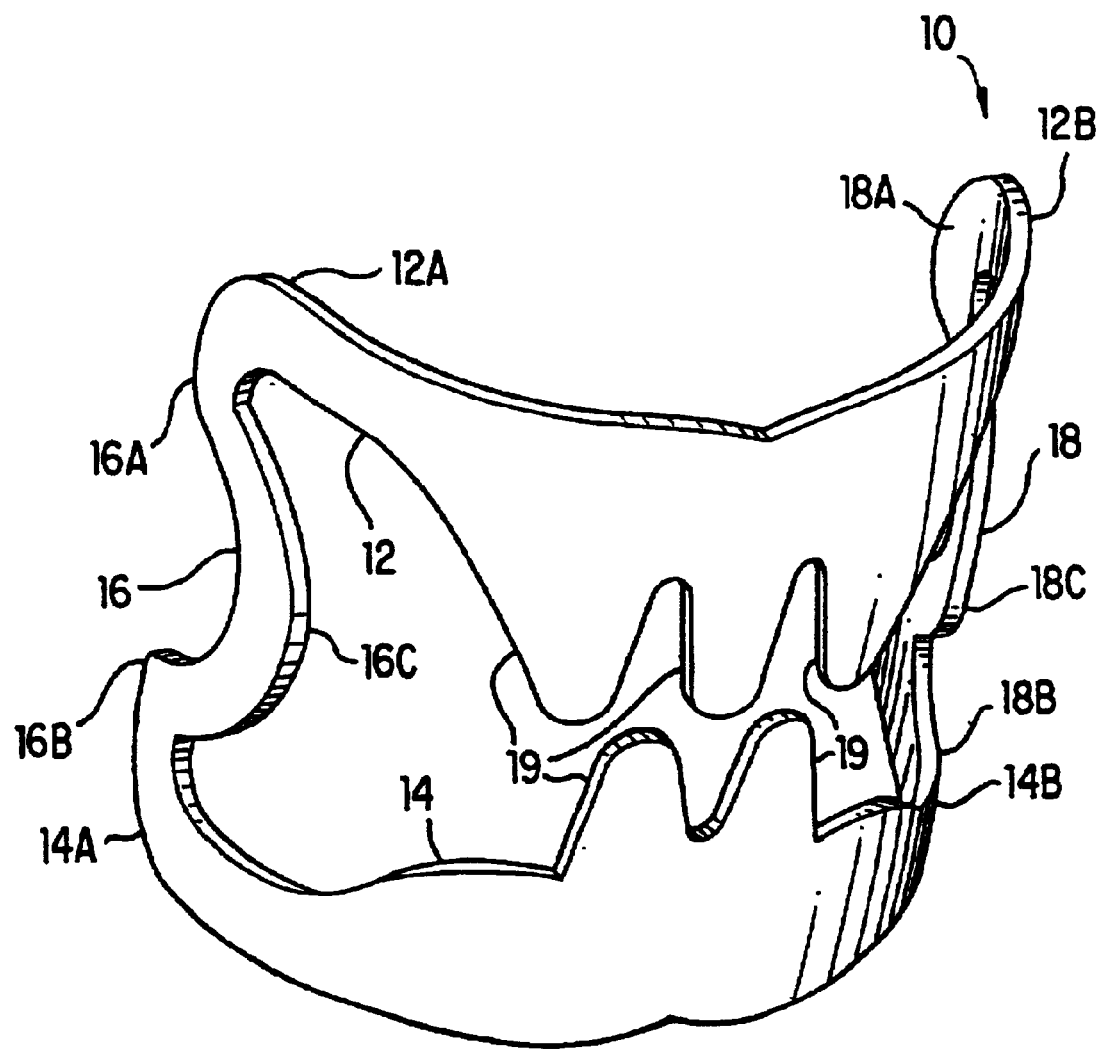
FIG. 1 is a perspective view of a first embodiment for a surgical clip in a tissue grasping position in accordance with the principles of the present invention.

FIG. 1 illustrates a first embodiment for a surgical clip that may be delivered to a site within a patient's body by an endoscopic device. The system and method for delivering surgical clip 10 to the wound site in the patient's body will be discussed later in this specification.

As can be seen in FIG. 1, surgical clip 10 is comprised of a first elongated tissue grasping surface 12 which has a first end 12A and a second end 12B and a second elongated tissue grasping surface 14 also having a first end 14A and a second end 14B. As can also be seen in FIG. 1, both the first tissue grasping surface 12 and the second tissue grasping surface 14 are formed by a semi-circular member.

A first joint 16 and a second joint 18 connect first elongated tissue grasping surface 12 to second elongated tissue grasping surface 14. First joint 16 is connected at a first end 16A to the first end 12A of first elongated tissue grasping surface 12 and at a second end 16B to the first end 14A of second tissue grasping surface 14. Similarly, second joint 18 is connected at a first end 18A to the second end 12B of first tissue grasping portion 12 and at a second end 18B to the second end 14B of second tissue grasping surface 14.

In this embodiment for surgical clip 10, the first joint 16 includes a semi-circular portion 16C which is disposed between first end 16A and second end 16B. Semi-circular portion 16C extends toward the first and second elongated tissue grasping surfaces. Similarly, second joint 18 also includes a semi-circular portion 18C between first end 18A and second end 18B and which also extends toward the first and second elongated tissue grasping surfaces. In this embodiment for surgical clip 10, both the first and second joints 16, 18, respectively, are formed integrally with the first and second tissue grasping surfaces 12, 14. As can also be seen in FIG. 1, each of the first and second tissue grasping surfaces includes interlocking teeth 19 which extend from a tissue grasping surface toward an opposing tissue grasping surface.

Figure 2:
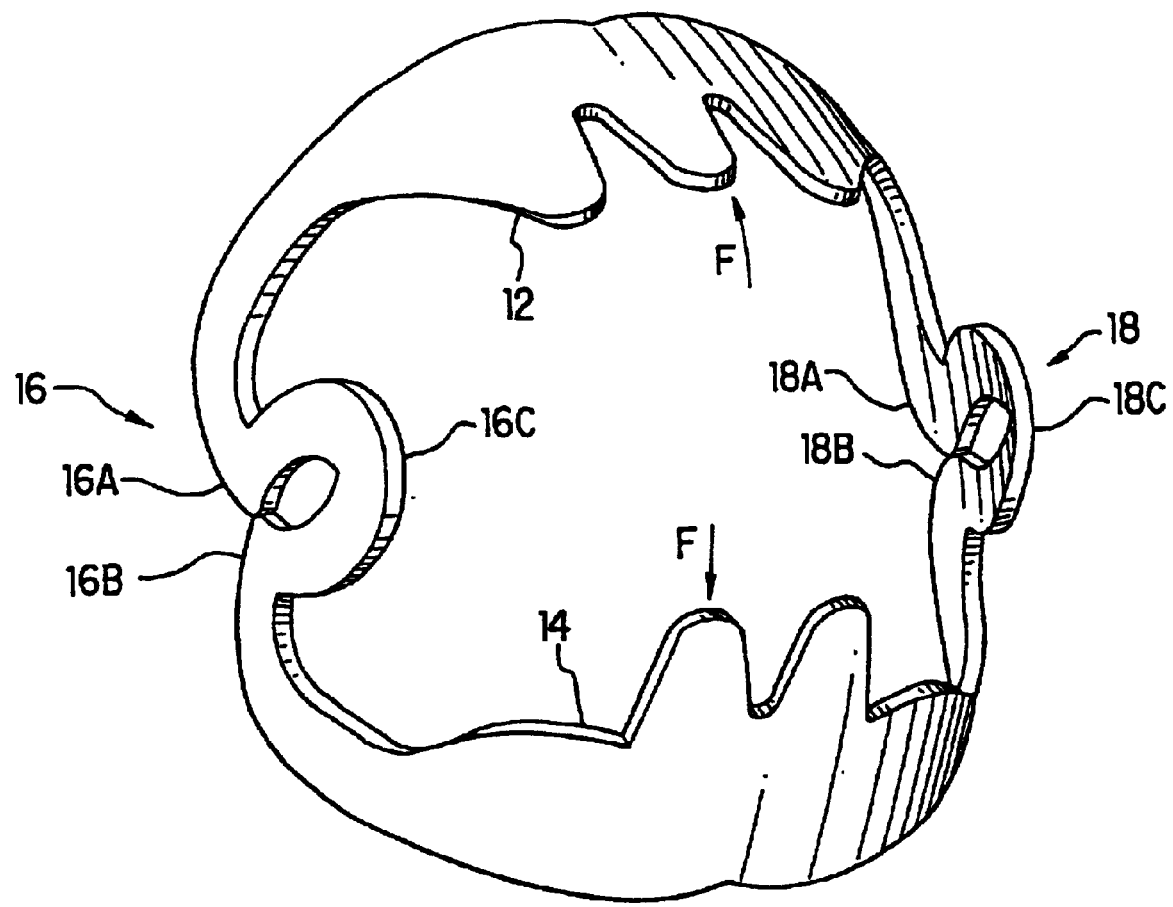
FIG. 2 is a perspective view of the surgical clip of FIG. 1 with the clip in a tissue receiving position.

First grasping portion 12 and second grasping portion 14 are movable with respect to each other between a tissue grasping position, as is illustrated in FIG. 1, and a tissue receiving position, as is illustrated in FIG. 2. When the first grasping portion 12 and second grasping portion 14 are in the tissue grasping position, body tissue is positioned between the first grasping portion 12 and the second grasping portion 14 to compress the body tissue between the two grasping surfaces. Teeth 19 engage the tissue and serve to assist in retaining the tissue between the two grasping surfaces.

Teeth 19 are not designed to cut through and sever the tissue, but rather, are designed to retain the tissue between the two grasping surfaces. The first and second joints 16, 18, respectively, bias the first tissue grasping surface 12 toward the second tissue grasping surface 14. Thus, in this embodiment for surgical clip 10, no additional force is required to be applied to first tissue grasping surface 12 and second tissue grasping surface 14 to compress body tissue between the two grasping surfaces. The total compression force required to enable first tissue grasping surface 12 and second tissue grasping surface 14 to be able to compress and retain tissue between them is solely provided by the biasing force of first joint 16 and second joint 18.

As can be seen in FIG. 2, the first grasping surface 12 and second grasping surface 14 are shown in their tissue receiving position. In order to position the first and second grasping surfaces in this orientation, a force F is applied against the grasping surfaces in the directions as illustrated in FIG. 2. This force is sufficient to overcome the biasing force of first joint 16 and second joint 18 which biases the first and second grasping surfaces toward each other in the tissue grasping position. As can be further seen in FIG. 2, when the first and second grasping surfaces are in their tissue receiving position, sufficient area is provided between the two grasping surfaces such that tissue can be received and grasped between the two grasping surfaces. When the grasping surfaces are in their tissue receiving position, it can be seen that first end 16A and second end 16B of first joint 16 engage with each other. Similarly, first end 18A and second end 18B of second joint 18 also engage with each other. However, it is not required that the respective first ends contact the respective second ends. All that is necessary is that sufficient area is provided between the two grasping surfaces such that tissue can be received and grasped between the two grasping surfaces. When first joint 16 and second joint 18 are in this configuration, the joints store within them an energy potential that, when force F is released from being applied against the first and second grasping surfaces, the joints return the first and second grasping surfaces to their tissue grasping position.

As will be explained further later in this specification, with surgical clip 10 in its tissue receiving position, it is placed on the outer surface of an endoscope cap which is included at a distal end of an endoscopic device. By positioning surgical clip 10 on the outer surface of the endoscope cap, the endoscope cap provides the force F that retains surgical clip 10 in its tissue receiving position. As will also be further explained later in this specification, once the endoscopic device, and thus surgical clip 10, are positioned adjacent to the wound area within the patient's body, the surgical clip 10 is deployed from the endoscope cap to the wound site. When the surgical clip 10 is deployed off of the endoscope cap, and thus the force F is no longer applied against the first grasping surface 12 and the second grasping surface 14, joints 16 and 18 will return the first and second grasping surfaces to the tissue grasping position which compresses the tissue that is positioned between the two grasping surfaces. Thus, by deploying the surgical clip 10 off of the endoscope cap, the body tissue, which is positioned between the first and second grasping surfaces, will be compressed between the grasping surfaces as a result of the biasing force applied to the grasping surfaces by the joints which connect the two grasping surfaces.

Surgical clip 10 may be comprised of a variety of different types of materials with the only requirement being that the material have the properties such that it is able to store an energy potential within it when the grasping surfaces are moved to their tissue receiving position and return the grasping surfaces to their tissue grasping position when the force that moves the grasping surfaces to their tissue receiving position is removed. The energy potential stored within the joints is released such that the grasping surfaces are biased toward each other to their tissue grasping position. One such material that could be utilized for first and second joints 16, 18, respectively, is a shape-memory alloy, such as a superelastic Nitinol. This material will provide the joint with a high mass/force ratio when compared to other biocompatible materials because there will be less yield losses during the process of opening the surgical clip 10 to its tissue receiving position. The use of a shape-memory alloy assumes that the austentite final ($A_f$) temperature is below the body temperature of the patient.

Although Nitinol may be a suitable material, there are numerous other materials that could also be utilized. Other examples of materials which could be utilized for the joints are titanium, stainless steel in a spring steel state, and high yield polymers. Stainless steel in a spring steel state could be utilized if the yield losses could be overcome, or if a multiple component design for the joints is employed, as will be discussed later in this specification. As mentioned previously, high yield polymers, as well as shape memory polymers and composites may also be utilized, especially in multiple component designs.

Figure 3:
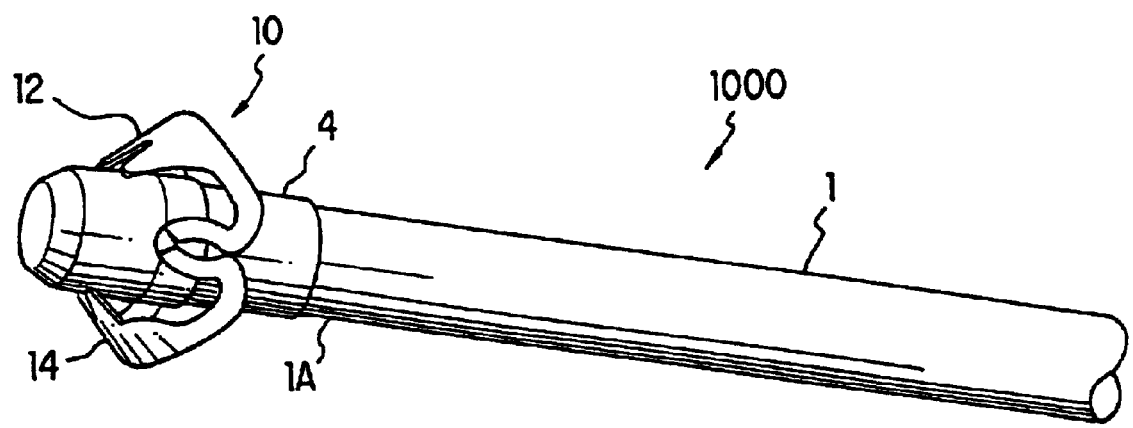
FIG. 3 is a perspective view of a first embodiment for a system for delivering a surgical clip to a surgical site within a patient's body to compress body tissue in accordance with the principles of the present invention.

FIG. 3 illustrates a first embodiment for a system for delivering a surgical clip to a wound site within a patient's body to compress the body tissue of the wound site. As can be seen, surgical clip 10 is disposed on an outer surface of endoscope cap 4. Endoscope cap 4 is disposed on the distal end 1A of an endoscopic device 1. As can be further seen, and as described previously, when surgical clip 10 is disposed on the outer surface of endoscope cap 4, first tissue grasping surface 12 and second tissue grasping surface 14 are in their tissue receiving position. The present invention is not limited to any particular type of endoscopic device or endoscope cap. As will be discussed later in this specification, the principles of the present invention may be utilized in performing any of a variety of different medical procedures and the present invention is not limited to any one particular type of procedure. The invention has utility in any medical procedure where it is desirable to compress body tissue at a wound site in order to assist in preventing hemorrhaging. Again, endoscope cap 4 may be any of a variety of known endoscope caps such as is used in variceal band ligation and snare mucosectomy where the target tissue is drawn into the space between the faces of the cap and the endoscopic device.

Figure 4:
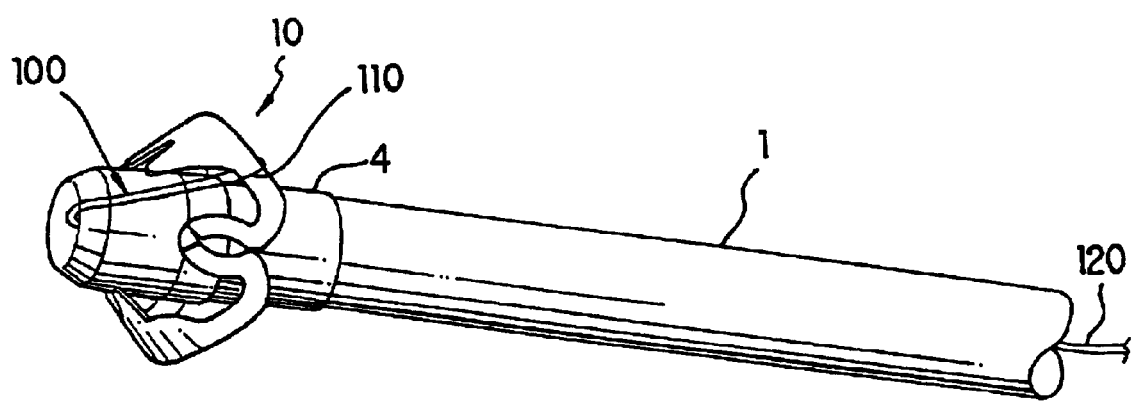
FIG. 4 is a perspective view of the system of FIG. 3 with a first embodiment of a deployment device for deploying the surgical clip from the endoscope cap.

As discussed previously, surgical clip 10 is deployed off of endoscope cap 4 after the surgical clip 10 has been positioned adjacent to the wound site. In order to deploy surgical clip 10 from endoscope cap 4, a variety of different types of deployment devices that are associated with surgical clip 10 may be utilized. FIG. 4 illustrates a first embodiment of a deployment device that may be utilized in the present invention. As can be seen in FIG. 4, a deployment device, or cable 100, is utilized in deploying surgical clip 10 from endoscope cap 4. As can be seen, a distal end 110 of cable 100 is looped around a portion of surgical clip 10. Cable 100 is then positioned through a working channel of the endoscopic device 1 where a proximal end 120 of cable 100 extends from a proximal end of the endoscopic device 1 which extends out of the patient's body. Thus, as can be understood, when the person who is performing the procedure pulls on the proximal end 120 of cable 100, which pulls cable 100 from a distal end to a proximal end of endoscopic device 1, surgical clip 10 will be pulled towards the distal end of endoscope cap 4 and thus off of endoscope cap 4 to deploy surgical clip 10 from the endoscope cap. This methodology is similar to variceal band ligation methods.

Figure 5:
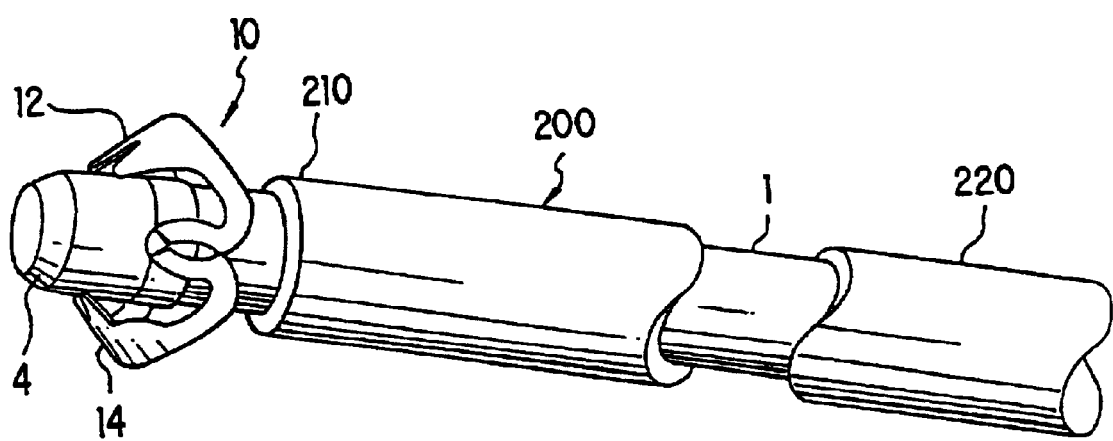
FIG. 5 illustrates a second embodiment for a deployment device.

FIG. 5 illustrates a second embodiment for a deployment device that may be utilized in the present invention. As can be seen in FIG. 5, the second embodiment for the deployment device is a tubular member 200 that is disposed around the endoscopic device 1. Tubular member 200 is movable on endoscopic device 1 between a position where distal end 210 of tubular member 200 does not engage with surgical clip 10 and a position where distal end 210 engages with surgical clip 10. By applying a force at proximal end 220 of tubular member 200, distal end 210 can be moved such that it engages with surgical clip 10. Further movement of tubular member 200 in a distal direction will deploy surgical clip 10 from endoscope cap 4. As can be understood, proximal end 220 of tubular member 200 extends outside of the patient such that a force may be applied to proximal end 220 to move tubular member 200 such that distal end 210 engages with surgical clip 10 to deploy surgical clip 10 from endoscope cap 4.

Figure 6:
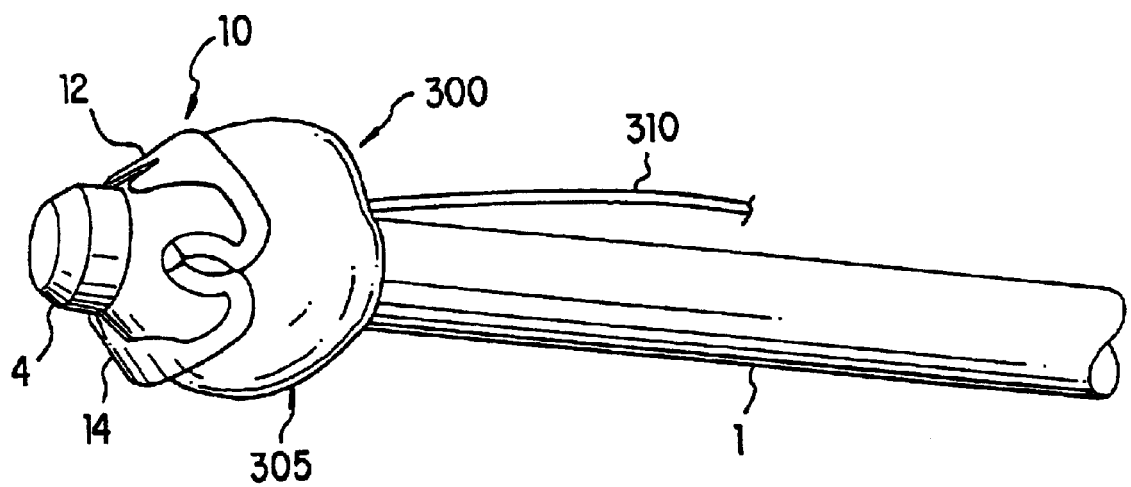
FIG. 6 illustrates a third embodiment for a deployment device and a first embodiment for an intubation mechanism in accordance with the principles of the present invention.

FIG. 6 illustrates a third embodiment for a deployment device. In the embodiment of FIG. 6, the deployment device comprises a balloon 300 where at least a portion of balloon 300 is disposed between surgical clip 10 and endoscope cap 4. An inflation lumen 310 extends from balloon 300 to a position outside of the patient such that pressure may be applied to balloon 300 to inflate balloon 300. Any substance may be utilized to inflate the balloon, including a gas, liquid, or any other substance. As can be understood, balloon 300 may be maintained in a state of inflation such that balloon 300 does not force surgical clip 10 off of endoscope cap 4. When the surgeon desires to deploy surgical clip 10 from endoscope cap 4, the surgeon would inflate balloon 300 to a state such that the inflation of balloon 300 causes surgical clip 10 to be moved toward the distal end of endoscope cap 4 such that continued inflation of balloon 300 will deploy surgical clip 10 off of endoscope cap 4.

As the balloon inflates, the force applied to surgical clip 10 serves two functions. First, as the balloon expands, surgical clip 10 also expands which helps to overcome the clamping force of the first and second grasping surfaces 12, 14, respectively, against the endoscope cap 4. As the surgical clip 10 radial force is reduced by the expanding balloon 300, the expanding balloon pushes, as described previously, surgical clip 10 off of endoscope cap 4 and onto the target tissue. An advantage of this methodology for deploying surgical clip 10 off of endoscope cap 4 is that there is no external force applied against the endoscope cap 4/endoscopic device 1/surgical clip 10 assembly such as is applied by the previously discussed embodiments for a deployment device, i.e., cable 100 or tubular member 200. Thus, deployment of surgical clip 10 from endoscope cap 4 by balloon 300 will help to reduce a possibility that the surgical instrument 1000 could be pushed away from the target wound site as a result of deploying surgical clip 10 from endoscope cap 4.

Similar in concept to the balloon deployment mechanism discussed previously, a force generator that is disposed around the endoscopic device 1 may be utilized to deploy surgical clip 10 from endoscope cap 4. The force generator may include various mechanisms for deploying surgical clip 10 from endoscope cap 4 and several of these alternatives will be discussed below.

Figure 7:
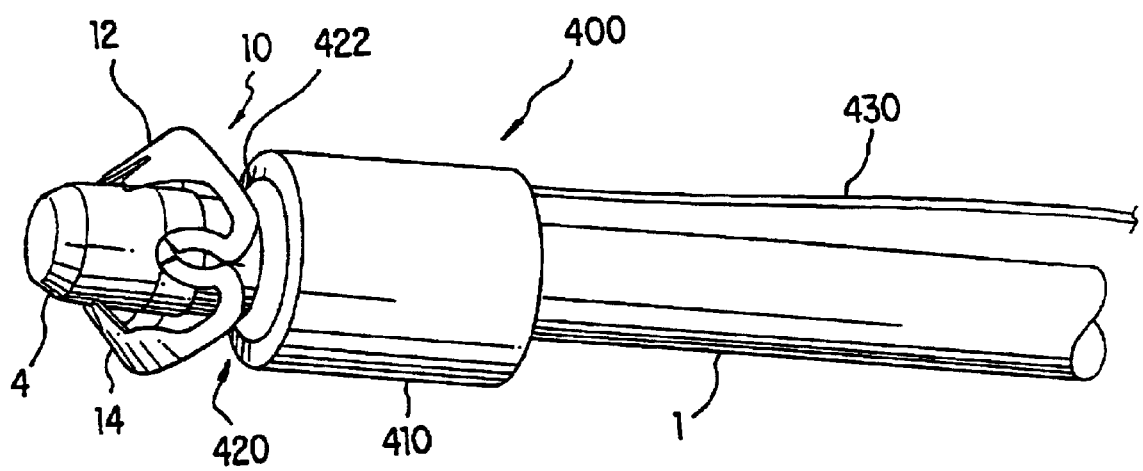
FIG. 7 illustrates a fourth embodiment for a deployment device.
Figure 8:
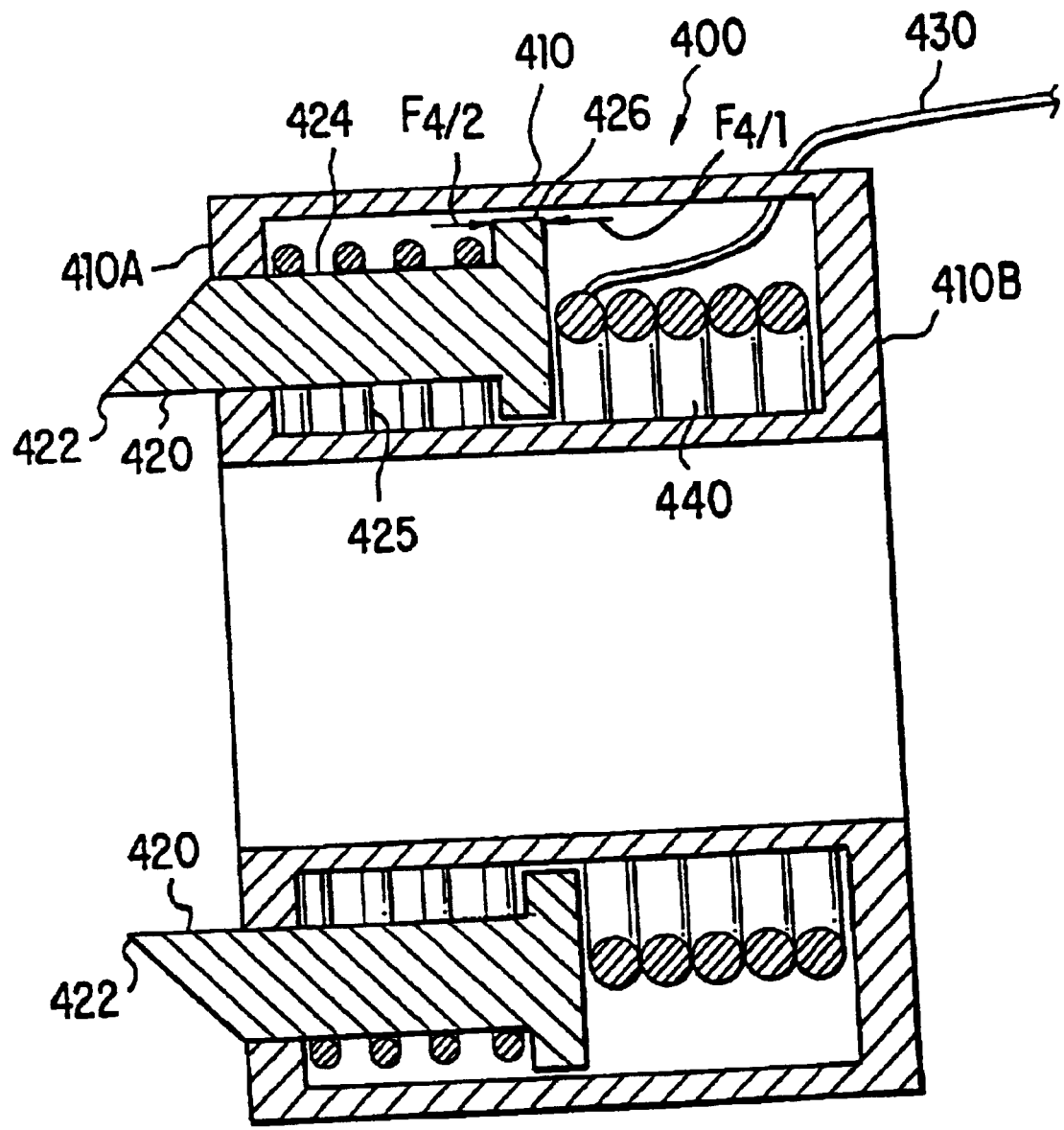
FIG. 8 is a cross-sectional view of the deployment device of FIG. 7.

FIG. 7 illustrates a fourth embodiment of a deployment device 400 that incorporates a force generator 410 that is disposed around endoscopic device 1 and is located proximal to surgical clip 10. As can be seen in FIGS. 7 and 8, force generator 410 includes an engagement member 420 that is at least partially disposed within the force generator 410 and which is movable between a first position where a distal end 422 of engagement member 420 does not engage with surgical clip 10 and a second position where distal end 422 of engagement member 420 engages with surgical clip 10. An actuator 440 is contained within force generator 410 for moving engagement member 420 to its second position where it engages with surgical clip 10.

FIG. 8 is a cross sectional view that further illustrates the fourth embodiment for deployment device 400 that includes force generator 410. As can be seen in FIG. 8, engagement member 420 is at least partially disposed within force generator 410. A retention spring 425 may be utilized to bias engagement member 420 in its first position where it does not engage with surgical clip 10. Retention spring 425 is positioned within force generator 410 such that it is disposed between a distal wall 410A of force generator 410 and piston 426 of engagement member 420. Thus, the tension spring 425 applies a force $F_{4/2}$ against piston 426 that biases engagement member 420 in its first position. Retention spring 425 is disposed around shaft 424 of engagement member 420. Actuator 440, in this embodiment, is a compression spring that is disposed within force generator 410 and between piston 426 and a proximal wall 410B of force generator 410. A cable 430, which extends from a position outside of the patient's body at a proximal end to a position within force generator 410 at a distal location, is attached to compression spring 440 to retain compression spring 440 in a compressed configuration. When cable 430 is released from compression spring 440, compression spring 440 applies a force $F_{4/1}$ against piston 426 of engagement member 420. The magnitude of force $F_{4/1}$ is greater than the force applied by retention spring 425, i.e., $F_{4/2}$. Thus, when cable 430 is released from compression spring 440, compression spring 440 acts upon piston 426 which in-turn extends distal end 422 of engagement member 420 such that it engages with surgical clip 10. As engagement member 420 continues its further extension from force generator 410 under the action of compression spring 440, engagement member 420 forces surgical clip 10 off of endoscope cap 4. As can be seen in FIG. 8, distal end 422 of engagement member 420 is formed in a tapered configuration such that distal end 422 is assisted in engaging with surgical clip 10 and forcing surgical clip 10 off of endoscope cap 4. The tapered surface of distal end 422 of engagement member 420 applies both a radial and linear force to the surgical clip.

Figure 9:
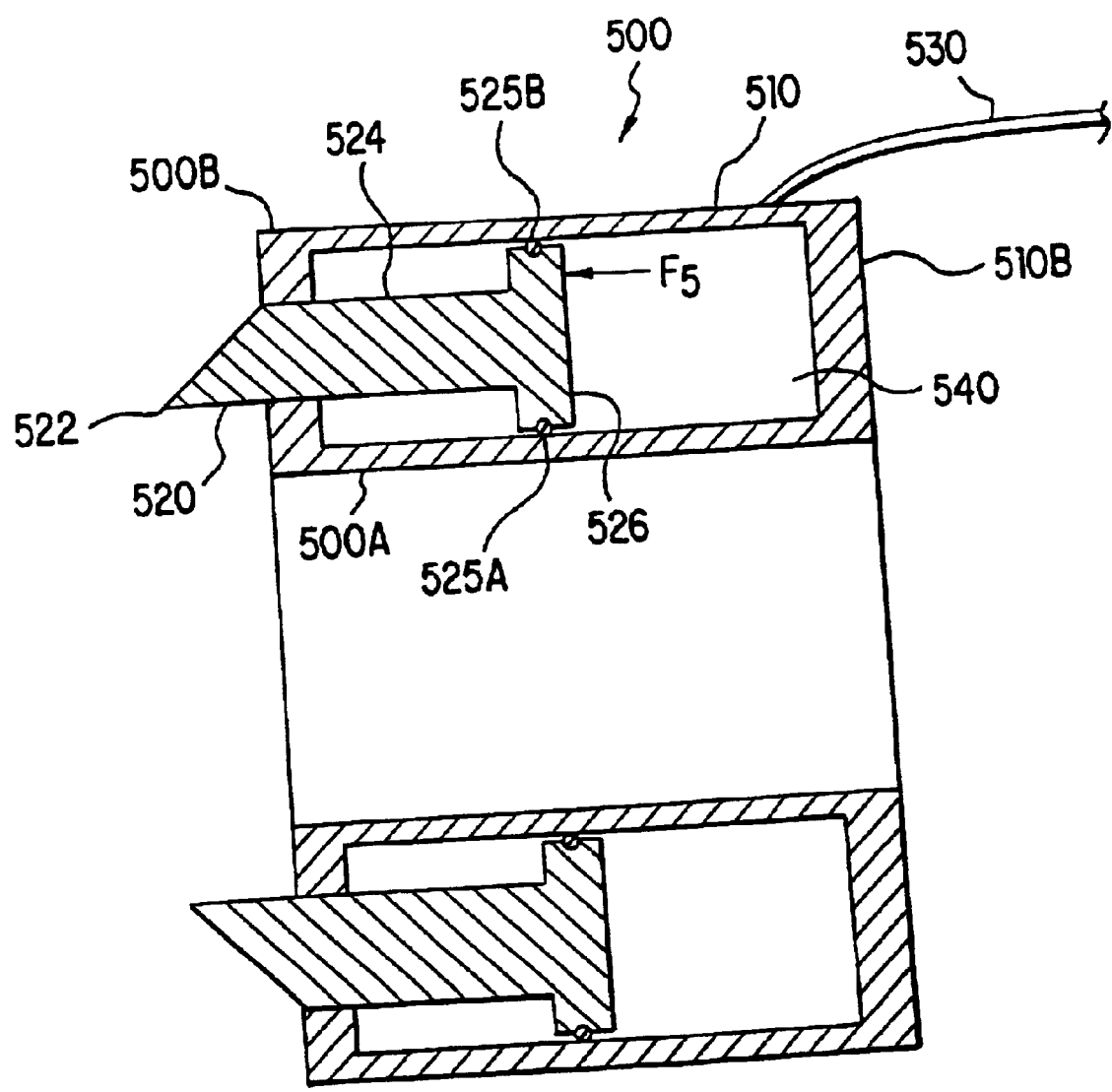
FIG. 9 is a cross-sectional view of a fifth embodiment for a deployment device.
Figure 10:
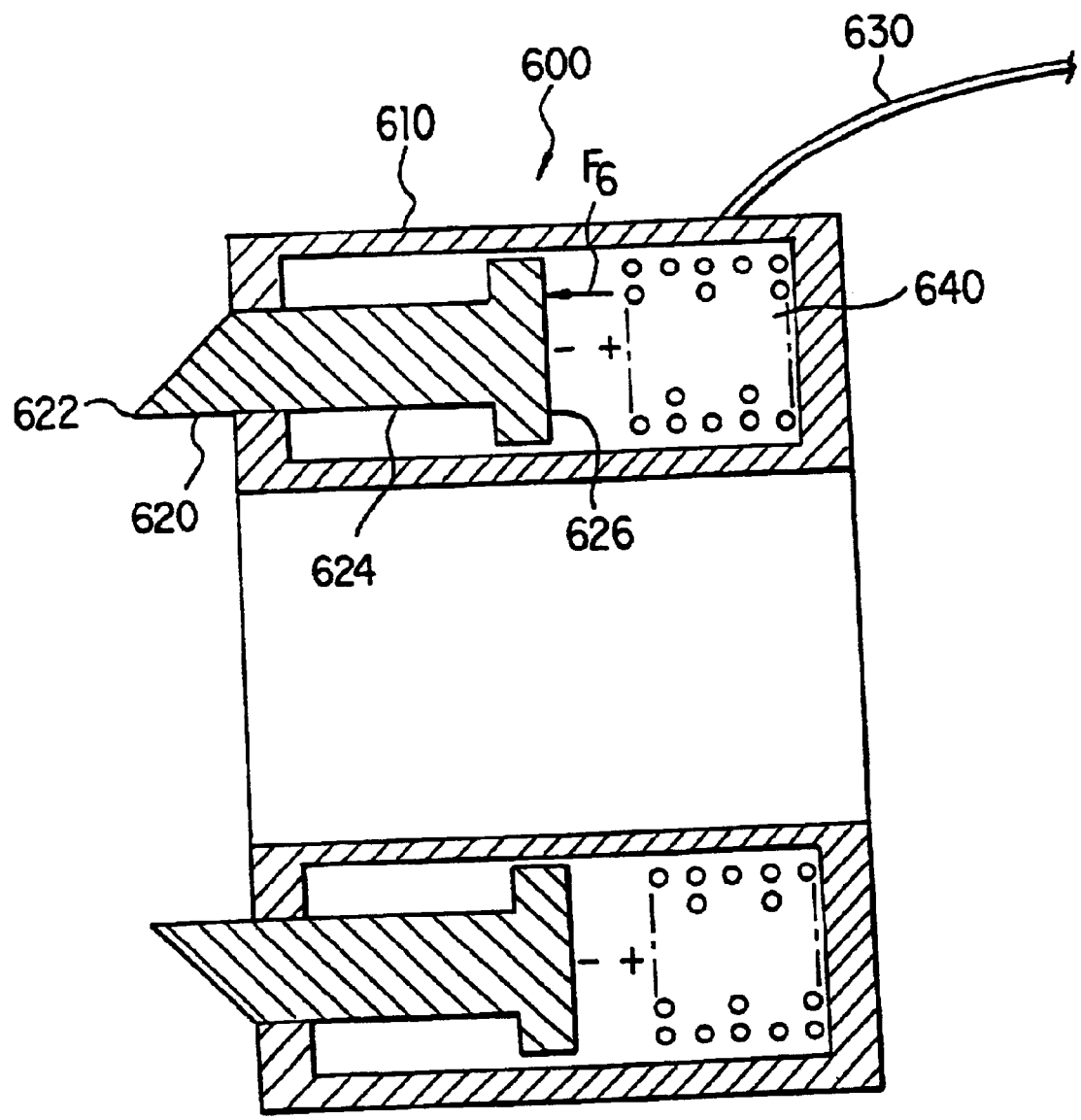
FIG. 10 is a cross-sectional view of a sixth embodiment for a deployment device.

FIGS. 9 and 10 illustrate alternative embodiments for the force generator. Whereas these alternative embodiments for the force generator do not illustrate a retention spring, it is to be understood that a retention spring as described above can be utilized in any of the additional embodiments contemplated for a force generator in order to provide a biasing force to assist in retaining the engagement member in its first position where it does not force surgical clip 10 off of endoscope cap 4. Additionally, whereas it has been described that the engagement member does not engage with the surgical clip when it is in its first position, it is not required that the engagement member does not engage with the surgical clip. All that is required is that the engagement member does not apply a force to the surgical clip that would tend to force the surgical clip off of the endoscope cap before it is desired to do so.

As stated above, FIGS. 9 and 10 illustrate alternative embodiments for a force generator which operate similar to the force generator previously discussed. The significant difference between the embodiments is the physical structure and operation of the actuator that is utilized to move the engagement member to its second position where it engages the surgical clip and deploys the surgical clip off of the endoscope cap.

FIG. 9, therefore, illustrates a fifth embodiment for a deployment device 500 that includes a force generator 510. Again, as discussed previously, force generator 510 operates similarly to force generator 410. As such, force generator 510 includes an engagement member 520 that includes a shaft 524, a piston 526, and a distal end 522 that engages with the surgical clip 10. However, force generator 510 utilizes an actuator for moving engagement member 520 that comprises a pressurizable chamber 540 that is disposed between piston 526 and proximal wall 510B of force generator 510. A pressure supply line 530 extends from a proximal end where it is located outside of the patient's body to a distal end where it is in communication with chamber 540. As chamber 540 is pressurized, a force $F_5$ is applied against piston 526 which moves engagement member 520 such that it will engage with the surgical clip and deploy the surgical clip off of the endoscope cap. In order to provide for a sealed chamber 540, a first seal 525A may be disposed between piston 526 and inside wall 500A of force generator 510 and a second seal 525B may be disposed between piston 526 and outside wall 500B of force generator 510. Thus, a sealed chamber 540 may be provided such that as the chamber is pressurized, piston 526 is moved within force generator 510.

Force generator 510 may utilize any of a variety of means for pressurizing the chamber, such as a gas or a liquid, and the present invention is not limited to any particular substance for pressurizing chamber 540. For example, the pressure can be supplied by injecting air into chamber 540 with a syringe. In an alternative embodiment, rather than utilizing pressure within chamber 540, a vacuum could be utilized to maintain the engagement member in a retracted position prior to deployment of the surgical clip.

FIG. 10 illustrates a sixth embodiment for deployment device 600 that utilizes a force generator 610 that incorporates an electrical coil 640 as the actuator for moving engagement member 620. As discussed previously, force generator 610 includes an engagement member 620 that has a shaft 624, a piston 626, and a distal end 622 that engages with the surgical clip. As can be seen, an electrical coil 640 is provided within force generator 610 at a location within force generator 610 that is proximal to piston 626. An electrically conductive cable 630 extends from electrical coil 640 proximally to a position where it exits the patient's body. Cable 630 provides a transmission means for energizing electrical coil 640. When electrical coil 640 is energized, it provides a force $F_6$ against piston 626 to move engagement member 620 such that its distal end 622 will engage with the surgical clip to deploy the surgical clip off of the endoscope cap. Thus, a current may be provided through cable 630 to electrical coil 640 to create an opposing charge against engagement member 620. As such, engagement member 620 could be a charged magnet or could be constructed of a ferrous metal.

The present invention is not limited to any particular structure for the force generator embodiments described above, in that, the force generators may be formed integrally with the endoscope cap or may be formed separate from the endoscope cap and disposed around the endoscope cap such that its engagement member is able to engage with the surgical clip. It may be advantageous to integrate the force generator, and thus the deployment force required, within the endoscope cap, however, the present invention is not limited to integrating the force generator within the cap.

As can be seen in FIGS. 11 through 13, the system for deploying a surgical clip within the patient's body may also include a tissue grasping device that may be disposed through a working channel of the endoscopic device. The present invention is not limited to any particular embodiment for a tissue grasping device and FIGS. 11 through 13 illustrate alternative embodiments for the tissue grasping device. The purpose of the tissue grasping device is to manipulate the target tissue that is to be compressed such that it is positioned within the endoscope cap. The tissue grasping device may be utilized in conjunction with suction that is applied to the tissue through the working channel of the endoscopic device. The suction would assist in positioning the target tissue within the endoscope cap. However, it is not required that one or the other of a tissue grasping device or a vacuum be utilized. In the present invention, either a tissue grasping device or suction, or a combination of the two, can be utilized with the present invention. All that is desired is that a mechanism be provided to assist in positioning the target tissue within the endoscope cap.

One advantage that would be possible if a grasping device that is passed through the working channel of the endoscopic device is used would be that this grasping device could also be used as a guide to push the endoscopic device to the wound site. Another advantage to utilizing a grasping device is that it could help to maintain the endoscopic device's position relative to the wound site during the surgical clip's deployment from the endoscope cap.

FIG. 11 illustrates a first embodiment for a tissue grasping device that could be utilized in the present invention. In FIG. 11, tissue grasping device 6 is illustrated as being disposed through a working channel (not visible) of the endoscopic device 1. It is noted that the endoscope cap and the surgical clip is not illustrated in FIGS. 11 through 13, however, based upon the previously provided discussion, it can be understood how these components would be configured on endoscopic device 1. Tissue grasping device 6 is illustrated as a solid tapered threaded member. With tissue grasping device 6, grasping of the targeted tissue would be accomplished by screwing the distal end of tissue grasping device 6 into the tissue. The screwing action could be accomplished either by rotating the entire sheath of the endoscopic device 1 or by rotating the tissue grasping device 6 within the sheath, e.g., analogous to a flexible drive shaft. When the device 6 is within the tissue, the tissue can be pulled within the endoscope cap. After deployment of the surgical clip, the tissue grasping device 6 would be unscrewed prior to removal of the endoscopic device 1.

FIG. 12 illustrates an alternative embodiment for a screw-shaped tissue grasping device 8. Tissue grasping device 8 functions similarly to the tissue grasping device 6 discussed in connection with FIG. 11, however, the design of tissue grasping device 8 is configured as a tapered spring-type of device as opposed to the solid tapered design of FIG. 11. However, tissue grasping device 8 is utilized in the same manner as was described for tissue grasping device 6.

FIG. 13 illustrates the sequential steps involved in utilizing a third embodiment for a tissue grasping device 9 as it is deployed into the organ wall of the targeted tissue. In the embodiment of FIG. 13, tissue grasping device 9 includes at least one J-shaped barb. In FIG. 13, a first barb 9A and a second barb 9B are illustrated. When the barbs are disposed within endoscopic device 1, the barbs are not formed in a J-shape but rather are forcibly configured in an elongated shape. Thus, the barbs are spring-formed into their J-shape and when the barbs are retracted into the endoscopic device 1, the barbs are elongated against the biasing force that wants to form them in their J-shape through interaction of the walls of endoscopic device 1 against the barbs.

When the endoscopic device 1 is placed against the targeted tissue, the sharp barbs are extended out of the endoscopic device 1, or out of a catheter included within endoscopic device 1 which contains the barbs, and into the tissue. When the barbs are extended from endoscopic device 1, the barbs pierce the organ wall and, since endoscopic device 1 is no longer restraining the ends of the barbs, as the barbs exit the endoscopic device and enter the targeted tissue the barbs reform their J-shape within the tissue and thus are able to engage with the tissue and retain the tissue on the J-shaped member. The barbs are formed with a sufficient amount of spring force to retain the J-shape in the barbs such that the barbs are able to lift and position the tissue within the endoscope cap. Again, after deployment of the surgical clip, the barbs may be retracted within the endoscopic device before the endoscopic device is removed from the patient's body. The present invention is not limited to any particular number of J-shaped barbs and any number of barbs can be utilized with the present invention.

As discussed previously, the present invention is not limited to any particular embodiment for a tissue grasping device and any of a variety of known grasper/forceps devices that are well-known in the art could be utilized with the present invention.

As can be seen in FIG. 3, surgical clip 10 extends radially from endoscope cap 4 such that it could possibly be desired to include in the present invention structures that could assist in intubating the system within the patient's body. As the endoscopic device, which is loaded with the surgical clip, is passed through, for example, the oral cavity, trachea and esophagus of the patient, it is desired that the surgical clip should not cause any injury to the patient. Several alternative embodiments for assisting in intubation are provided.

Referring back to FIG. 6, balloon 300 may also be utilized to assist in intubation as well as for use in deploying surgical clip 10. For assisting in intubation, balloon 300, which is located proximal to surgical clip 10, could be inflated to a diameter which exceeds the radially extending diameter of surgical clip 10. Thus, the balloon 300 would ride against the lumen wall which would keep the surgical clip 10 out of contact with the lumen wall. The balloon 300 could be partially inflated so as not to deploy surgical clip 10 but yet provide for assisting in intubation of surgical clip 10 within the patient's body. As such, when the balloon 300 is partially inflated, the balloon has a diameter at a portion 305 of the balloon which is located proximal to surgical clip 10 which is greater than a diameter of the surgical clip.

Figure 14:
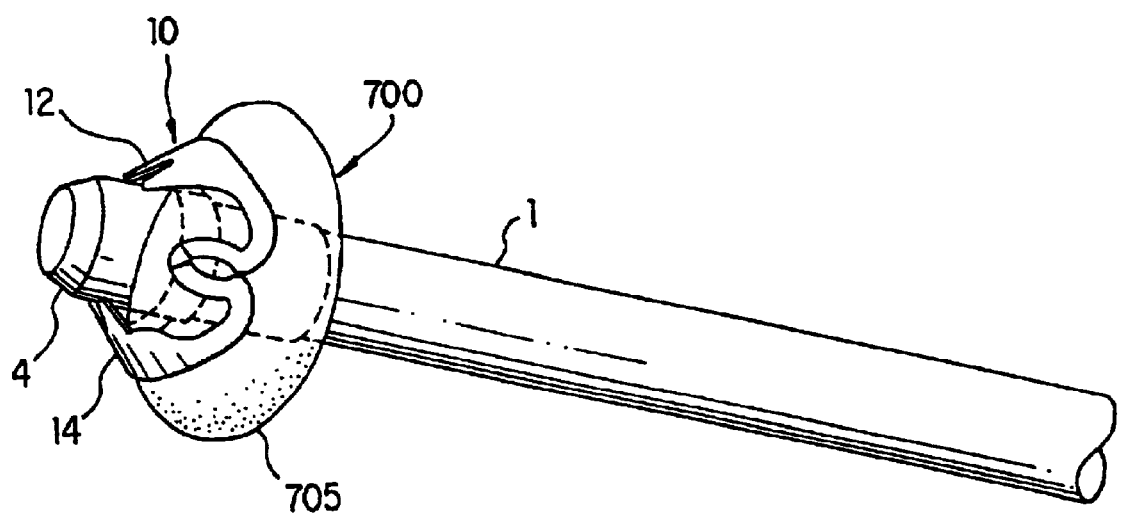
FIG. 14 illustrates a second embodiment for an intubation mechanism.

An alternative embodiment for a device to assist in intubation which would function similar to the balloon discussed previously is illustrated in FIG. 14. FIG. 14 illustrates a second embodiment for an intubation mechanism 700. Intubation mechanism 700 is comprised of a foam member that is disposed on the endoscope cap 4. Alternatively, foam member 700 could be formed integral with endoscope cap 4. The foam member 700 has a diameter at a portion 705 of foam member 700 which is located proximal to surgical clip 10 which is greater than the diameter of surgical clip 10. Thus, as the surgical clip is inserted into the body of the patient, the greater diameter of foam member 700 would prevent the surgical clip from harming the lumen through which the surgical clip is inserted.

Figure 15:
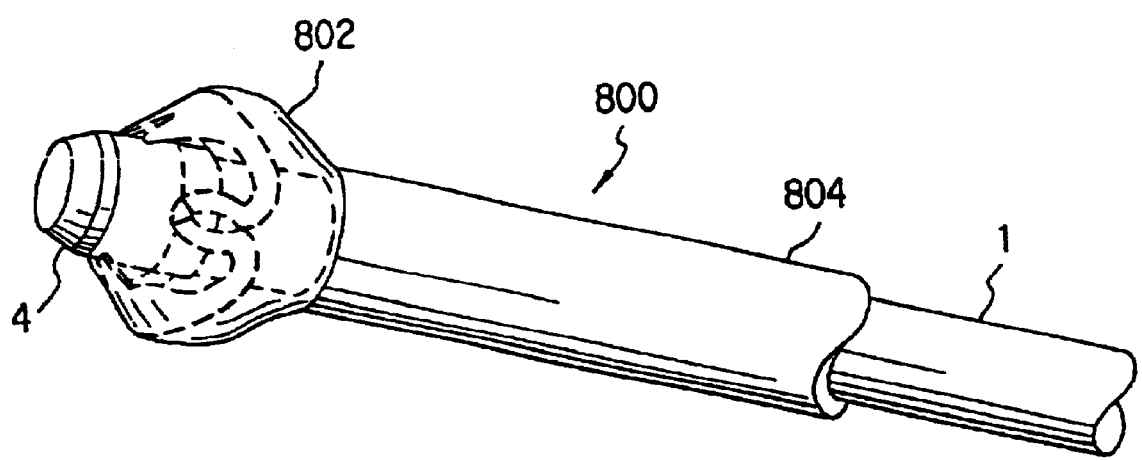
FIG. 15 illustrates a third embodiment for an intubation mechanism.

FIG. 15 illustrates a third embodiment for an intubation mechanism 800 that could be utilized with the present invention. Intubation mechanism 800 is comprised of a retractable cover 802 which is attached to a tubular member 804. Cover 802 is movable by moving tube 804 between a first position where cover 802 covers surgical clip 10 and a second position where cover 802 is not disposed over surgical clip 10. By covering surgical clip 10 with cover 802, the walls of the lumen are protected from potential injury from surgical clip 10. The cover 802, which is attached to a tubular member which could be similar to that described in FIG. 5, could be slid back from covering surgical clip 10 after intubation, when the targeted lesion is visualized.

Alternatively, cover 802 could be integrated into the second embodiment for the deployment device as illustrated in FIG. 5 which comprised tubular member 200. In this embodiment where a cover was integrated into a tubular deployment device, the cover would not be retracted until after the surgical clip is deployed by the tubular member.

Figure 16:
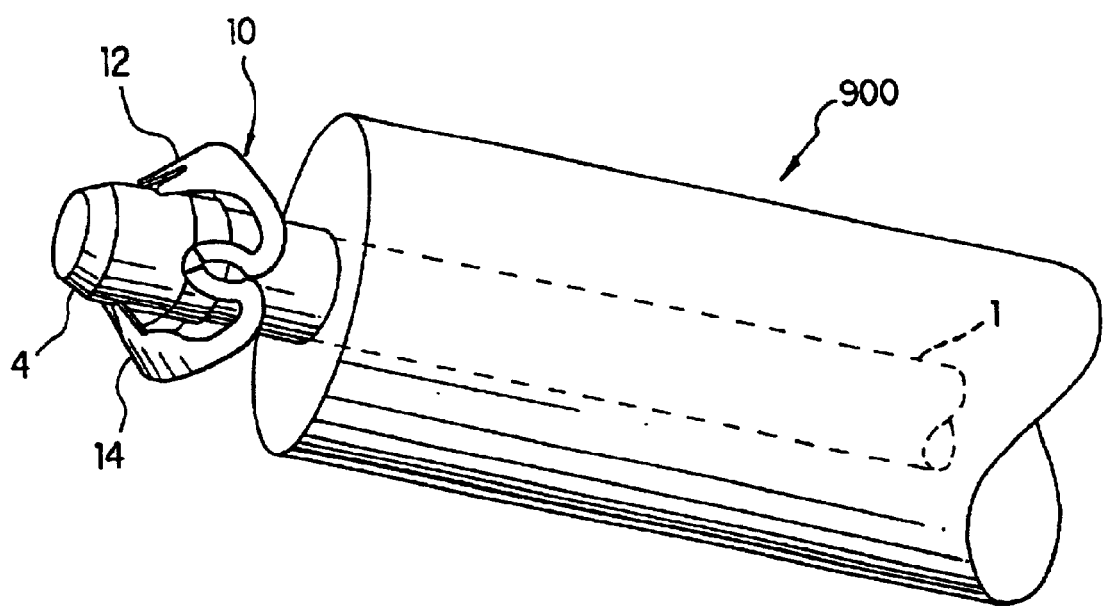
FIG. 16 illustrates a fourth embodiment for an intubation mechanism.

FIG. 16 illustrates a fourth embodiment for an intubation mechanism 900. As illustrated in FIG. 16, an intubation overtube 900, which is well-known in the art and which would extend from, for example, the oral cavity into the gastric or duodenal bulb could also be utilized to protect the lumen walls. The overtube could be placed prior to intubation over the surgical clip-loaded endoscopic device. An advantage to this embodiment for an intubation mechanism is the relatively easy multiple intubations possible if multiple clips are required. Another advantage is that the overtube could include working lumens that could be utilized to irrigate, aspirate, and provide access for secondary devices. A third advantage could be that the overtube could provide additional support for the endoscopic device during deployment, which could assist in overcoming a force opposing movement of the endoscopic device.

Further description will now be provided of an embodiment for the procedure for deploying the surgical clip in accordance with the principles of the present invention. First, the target ulcer or lesion is diagnosed visually with the endoscopic device by the clinician. After diagnosis, the endoscopic device is withdrawn and the endoscope cap, which is loaded with the surgical clip, is attached to the endoscopic device. It is noted that other factors may make the clinician decide before the diagnostic intubation that bleeding is occurring which would possibly prompt the clinician to load the surgical clip onto the endoscopic device prior to diagnostic intubation.

The endoscope is manipulated such that it is positioned near the wound site. If here is active bleeding, the clinician may irrigate the wound using the working channel of the endoscope to improve visualization. If there is active bleeding, or if a rupture could be imminent, the clinician may decide to inject a sclerosing/vasoconstricting drug by needle therapy through the working channel of the endoscope. The goal of such being to maintain a temporary, clear field of view during the process of applying the surgical clip. The drug delivery device could also be used to clear the field with irrigation. It is also possible that the clinician may decide to pretreat the wound site with a thermal device (including irrigation) for the same reasons. Additionally, it is also possible that the clinician may decide to utilize injection and/or thermal therapy as a combination treatment with the surgical clip.

When the decision to apply the surgical clip is made, the target tissue, as discussed previously, first needs to be manipulated within the endoscope cap. The working channel of the endoscope can now be utilized for tissue manipulation. The endoscope cap can be manipulated proximate to, and against the wound site, before suction is applied through the working channel to aspirate the tissue into the endoscope cap and maintain scope position during the deployment of the surgical clip. As also discussed previously, a tissue grasping device can be passed through the working channel of the endoscope to grasp and pull the tissue into the endoscope cap. After grasping the tissue, the tissue grasping device can also be used as a guide to push the endoscope to the wound site. As also discussed previously, another advantage to this grasping technique is that it will help to maintain the scope's position during the deployment of the surgical clip. Again, grasping and aspiration may also be used in combination.

When the target tissue is within the endoscope cap, the surgical clip is deployed off of the end of the endoscope cap, thus compressing the tissue surrounding the wound to create the desired mechanical compression.

The surgical clip, in this procedure, is not intended to be a permanent implant. It is intended to remain in-place until permanent healing is attained, which may be a period of between 48 hours to two weeks. The surgical clip is intended to slough off over time due to the tissue that is compressed within the surgical clip dying from the loss of blood supply to the tissue and/or a slow cutting action applied by the surgical clip itself to the tissue. After sloughing off, the surgical clip is passed as part of the patient's normal digestion. The surgical clip's depth of penetration should be well into the submucosa, but not through the muscularis to perforate into the peritoneum.

The surgical clip is primarily intended to be successfully deployed and effect hemostasis in a single application. However, a failed deployment, poor location, or a large lesion could require application of multiple surgical clips. Should multiple clips be required, additional clips could be reloaded onto the endoscope cap during the procedure. For example, a surgical clip could be deployed and then the endoscopic device could be removed from the patient's body. A second surgical clip could then be loaded onto the endoscopic device. The reloaded endoscopic device could then be reinserted into the patient's body for deployment of the second surgical clip. It is also contemplated that the present invention could incorporate multiple surgical clips that are preloaded for deployment on the endoscopic device and deployed in a single intubation procedure. These multiple preloaded clips could be deployed in a manner similar to that as utilized in multiple firing band ligation devices.

An alternative procedure is contemplated for deploying the surgical clip. As described previously, the surgical clip has been described as being comprised of a shape-memory alloy that is deployed within the body in an austentite final phase, i.e., where the material of the joints are formed such that they fully store energy such that the first and second grasping surfaces are returned to their tissue grasping position when the surgical clip is deployed from the endoscope cap. However, the shape-memory alloy could also be used effectively for comprising the surgical clip by deploying the surgical clip in some level of the martensite phase, or "soft" phase, where the joints are formed such that they do not fully store an energy potential within them in this phase for the shape-memory material. By loading the surgical clip in a martensite phase, it could assist in deploying the surgical clip by reducing the force as applied on the endoscope cap by the surgical clip prior to deployment of the surgical clip. As can be understood, when the surgical clip is deployed on the endoscope cap, the first and second grasping surfaces of the surgical clip, because they are normally biased toward each other, apply a force on the endoscope cap. Thus, this force applied by the surgical clip on the endoscope cap could be disadvantageous when applying the force to deploy the surgical clip from the endoscope cap. Therefore, if the surgical clip is positioned on the endoscope cap in a martensite phase, the force applied to the endoscope cap by the surgical clip would not be as great and thus, deployment of the surgical clip off of the endoscope cap could be accomplished more easily. However, if this change in material phase for the surgical clip is utilized in the present invention, an alternative procedure for deploying the surgical clip would be utilized.

The alternative procedure for deploying the surgical clip off of the endoscope cap where the surgical clip was positioned on the cap in a martensite phase encompasses loading the surgical clip onto the cap in its "soft" phase. The tissue is then manipulated into the endoscope cap, as described previously. The surgical clip is then deployed by any of the deployment mechanisms described previously where, after deployment of the surgical clip, the surgical clip softly compresses the targeted tissue. The endoscopic device is slightly retracted from the wound site and the surgical clip is then heated to a temperature that is above the austenite final ($A_f$) temperature by, for example, applying hot water through the endoscope or by applying a heating current to the surgical clip with a secondary heating device that could be deployed through the endoscope, e.g., snares, hot forceps, etc. Preferably, the martensite start ($M_s$) temperature will be below body temperature. Advantageously, electrical heating can provide a secondary benefit in the procedure by cauterizing the tissue.

Whereas a first embodiment for surgical clip 10 has been discussed, the present invention is not limited to any particular embodiment or size for the surgical clip. The size of the surgical clip may vary for use in different procedures and on different endoscopic devices. FIGS. 17 through 33, which will be discussed below, illustrate alternative embodiments for a surgical clip in accordance with the present invention.

Figure 17:
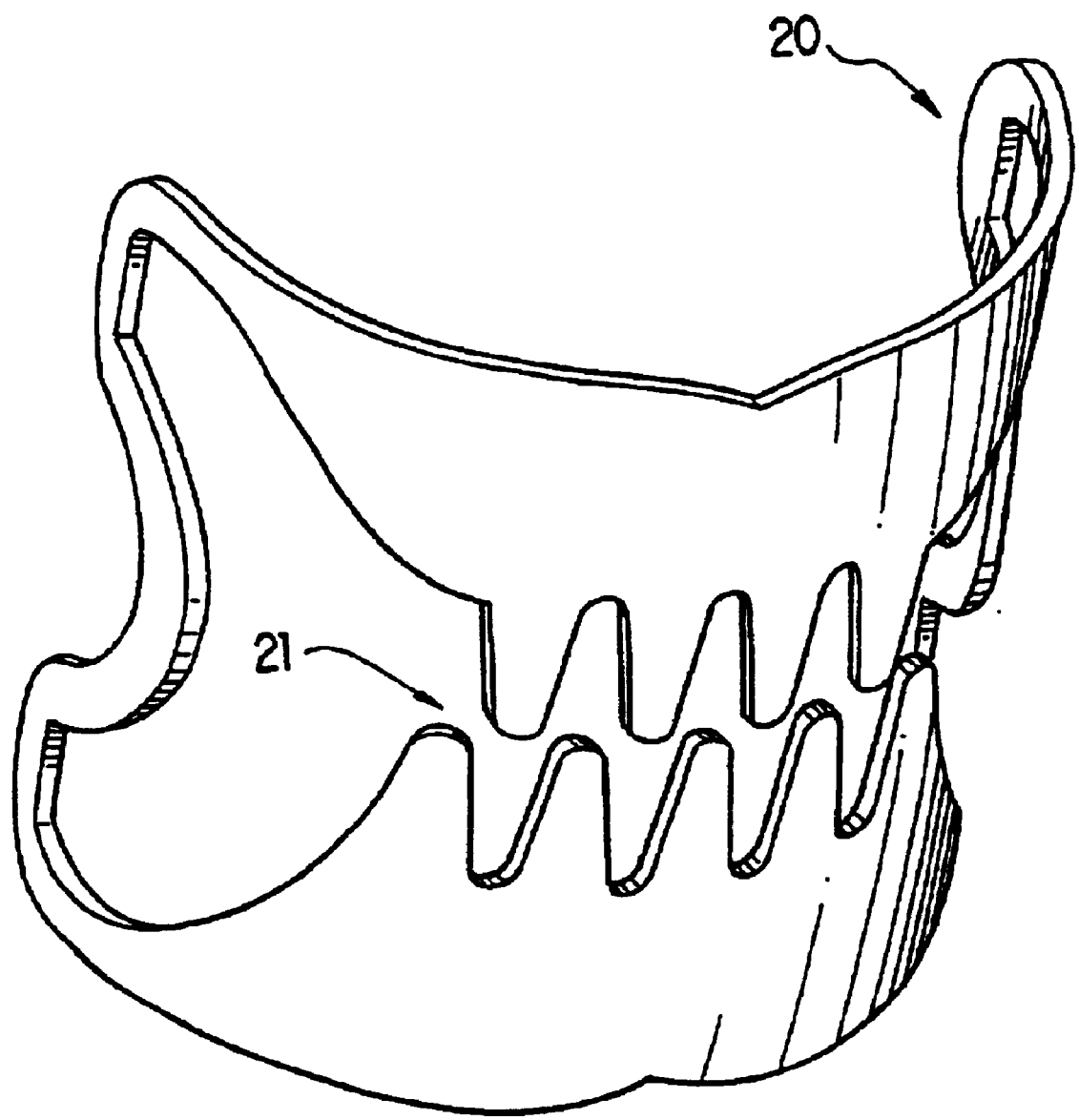
FIG. 17 illustrates a second embodiment for a surgical clip that includes a different quantity of teeth than the embodiment illustrated in FIG. 1.

FIG. 17 illustrates a second embodiment for a surgical clip 20 in accordance with the principles of the present invention. As can be seen in FIG. 17, as opposed to the first embodiment of surgical clip 10 illustrated in FIG. 1, surgical clip 20 includes a greater number of teeth 21. Thus, the present invention is not limited to any particular number of teeth that are included on the first and second grasping surfaces. Additionally, the size and form of the teeth may vary. For example, a single, flat, tooth may be provided on each grasping surface as opposed to a plurality of teeth on each grasping surface. Providing a single, flat, tooth may be preferred if a high clamping force is provided to the surgical clip. Alternatively, instead of teeth, the interface between the two grasping surfaces may be formed more as waves or shallow teeth with a large pitch. Again, the present invention is not limited to any particular number or configuration of teeth. The only consideration is that the interface between the first and second grasping surfaces provide a holding force that prevents the surgical clip from migrating off of the tissue that is to be compressed but yet not be so invasive as to tear through the tissue prematurely.

Figure 18:
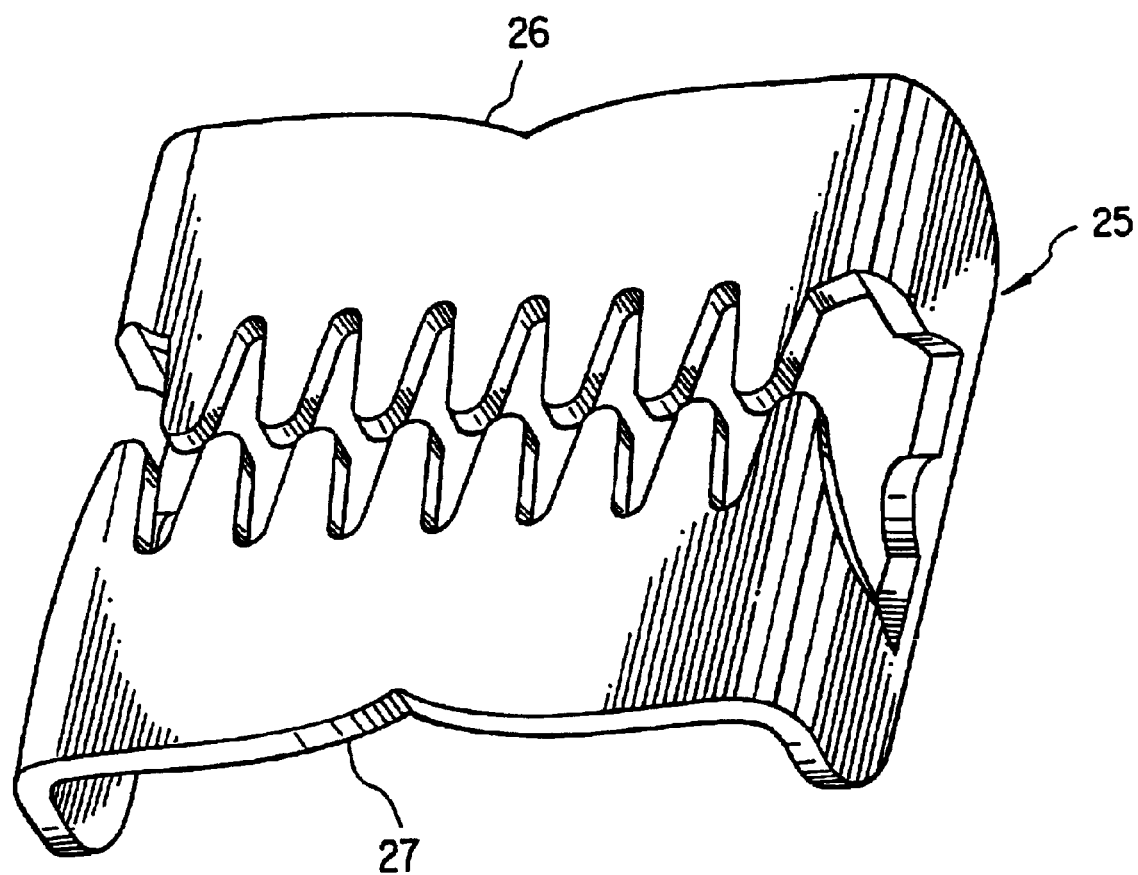
FIG. 18 illustrates a third embodiment for the surgical clip with the tissue grasping surfaces formed as straight members.

FIG. 18 illustrates a third embodiment for surgical clip 25. As can be seen, surgical clip 25 includes first and second grasping portions 26, 27, respectively, which are formed as straight members which is in contrast to the embodiment of FIG. 1 where the first and second grasping portions were formed as semi-circular members. Thus, the grasping portions may be formed in a variety of configurations which may have wider or narrower widths. A benefit of including wide grasping portions in a flat configuration as illustrated in FIG. 18 is for use in treating larger wound sites.

Whereas the embodiments discussed previously for the surgical clip illustrate grasping portions that define a slight gap between them when they are in their tissue grasping position, which may be preferred to allow for space to receive the tissue, alternatively, the opposing grasping portions could be normally closed, i.e., engaging with each other, with the clamping force lessened in order to compress tissue between the grasping surfaces without cutting through the tissue prematurely.

Figure 19:
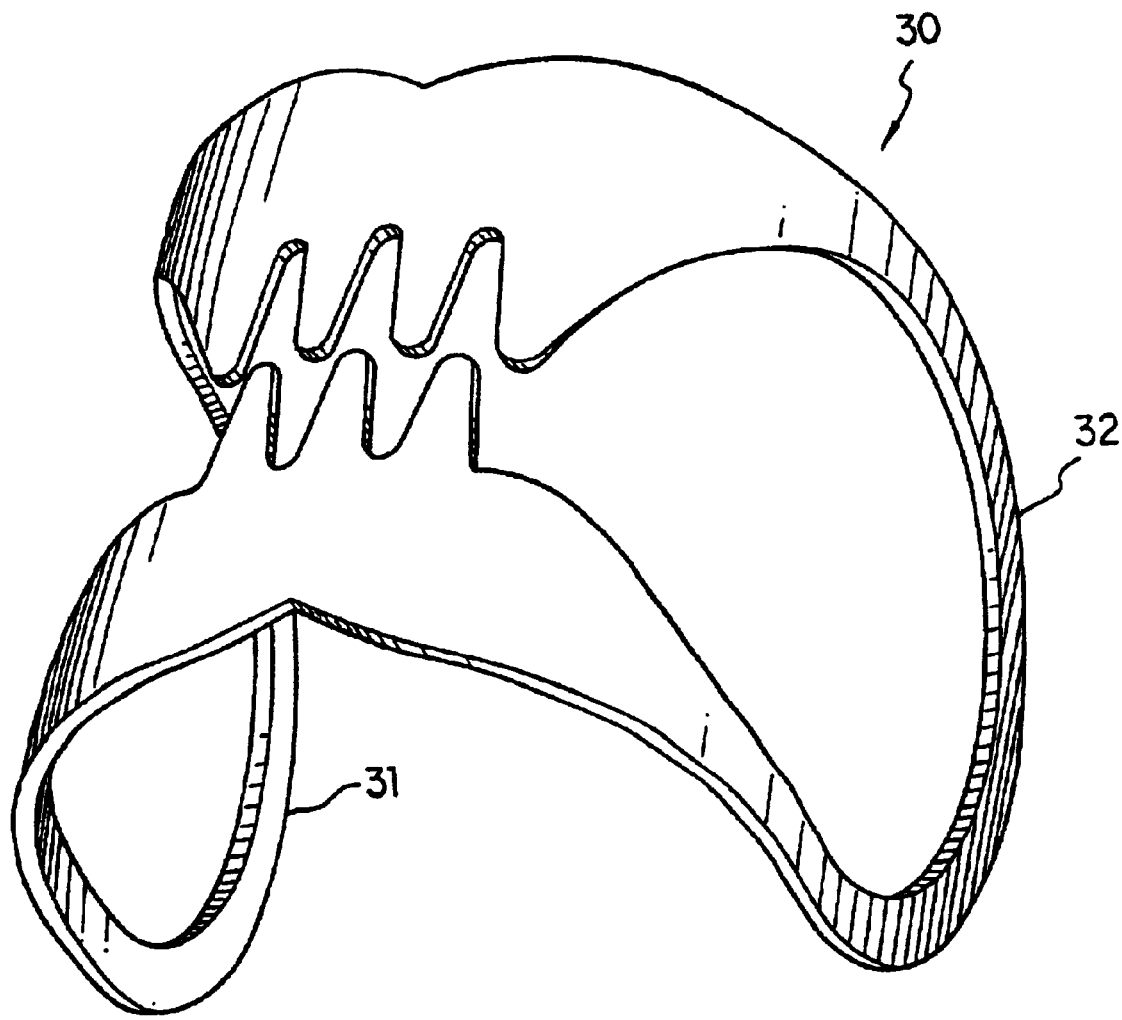
FIG. 19 illustrates a fourth embodiment for the surgical clip with enlarged joints.
Figure 20:
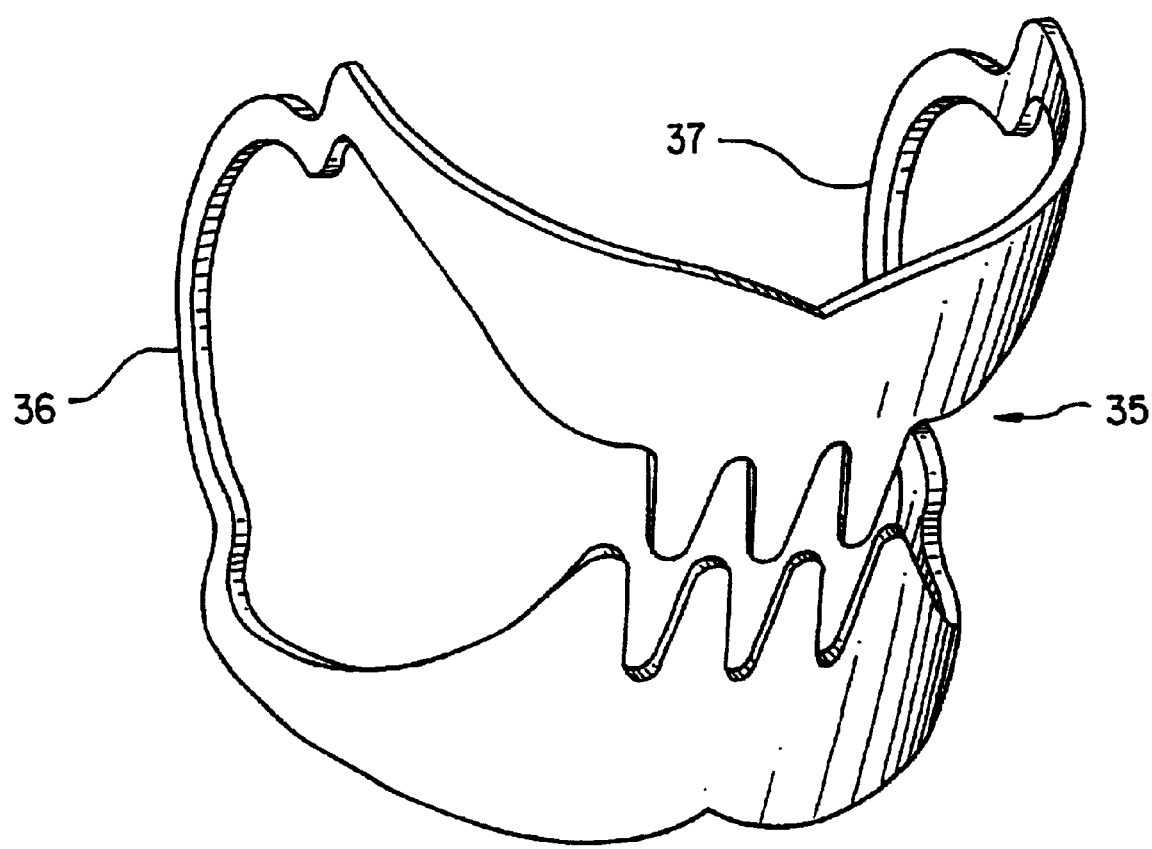
FIG. 20 illustrates a fifth embodiment for the surgical clip with enlarged joints.

Various alternative designs for the joints which interconnect the two grasping surfaces are also contemplated. These alternative joint designs can provide for application of different forces which may be preferable, provide for use of the surgical clip in other surgical procedures, or to allow for use of different materials in forming the joints. FIGS. 19 and 20 illustrate an alternative joint design where the joint is enlarged in comparison to the joint illustrated in the first embodiment of surgical clip 10 illustrated in FIG. 1. Additionally, the semi-circular portion of the joints of FIGS. 19 and 20 extend outwardly or away from the grasping surfaces.

As can be seen in FIG. 19, first joint 31 and second joint 32 of surgical clip 30 are larger in size than that previously described. Similarly, as illustrated in FIG. 20, first joint 36 and second joint 37 of a fifth embodiment for surgical clip 35 are also enlarged when compared to the first embodiment of surgical clip 10. By enlarging the joint, the joint spreads the opening yield force over more joint material. This may be advantageous where lower yield materials are utilized to comprise the joints.

Figure 21:
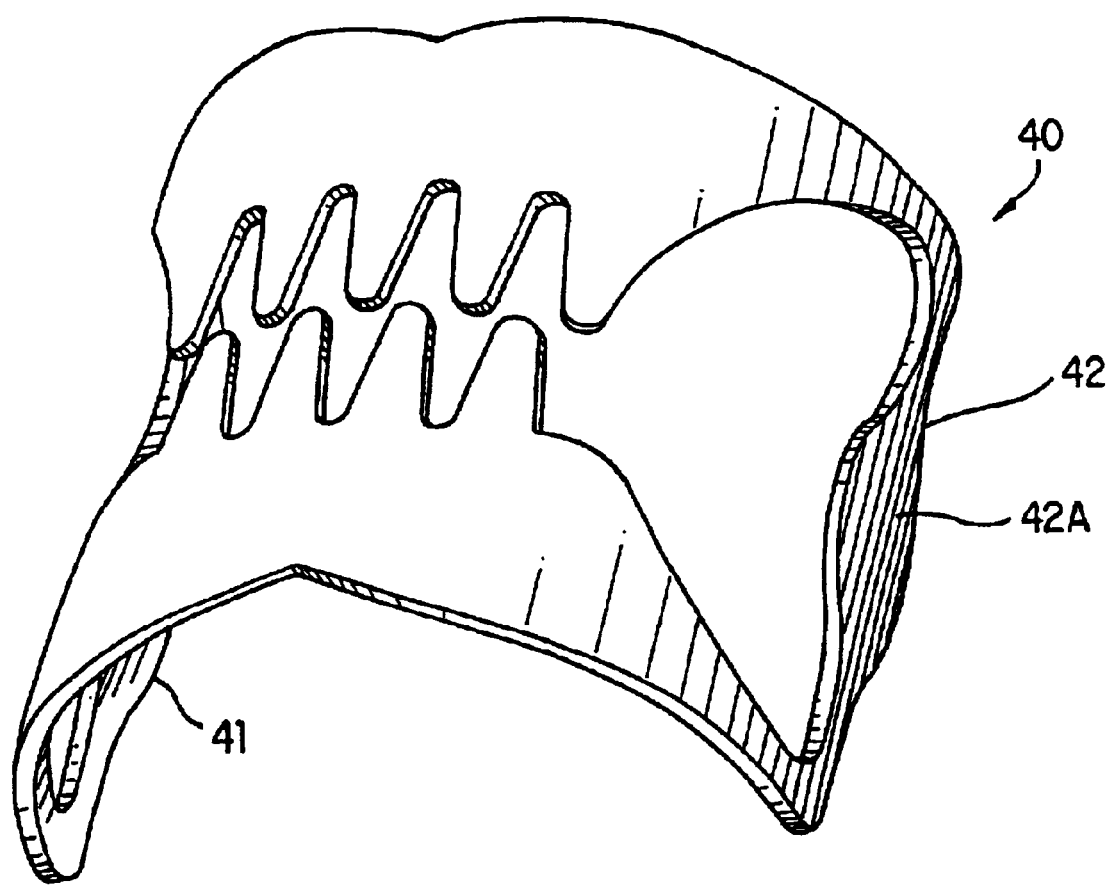
FIG. 21 illustrates a sixth embodiment for the surgical clip which includes additional structure at a center point of each joint.

FIG. 21 illustrates a sixth embodiment of a surgical clip 40 that includes an alternative joint design. As can be seen in FIG. 21, second joint 42 includes additional material to the joint centerpoint 42A. First joint 41 is similarly formed. The provision of additional material to the joints' centerpoint could increase the clamping force that is able to be provided by the joints.

Figure 22:
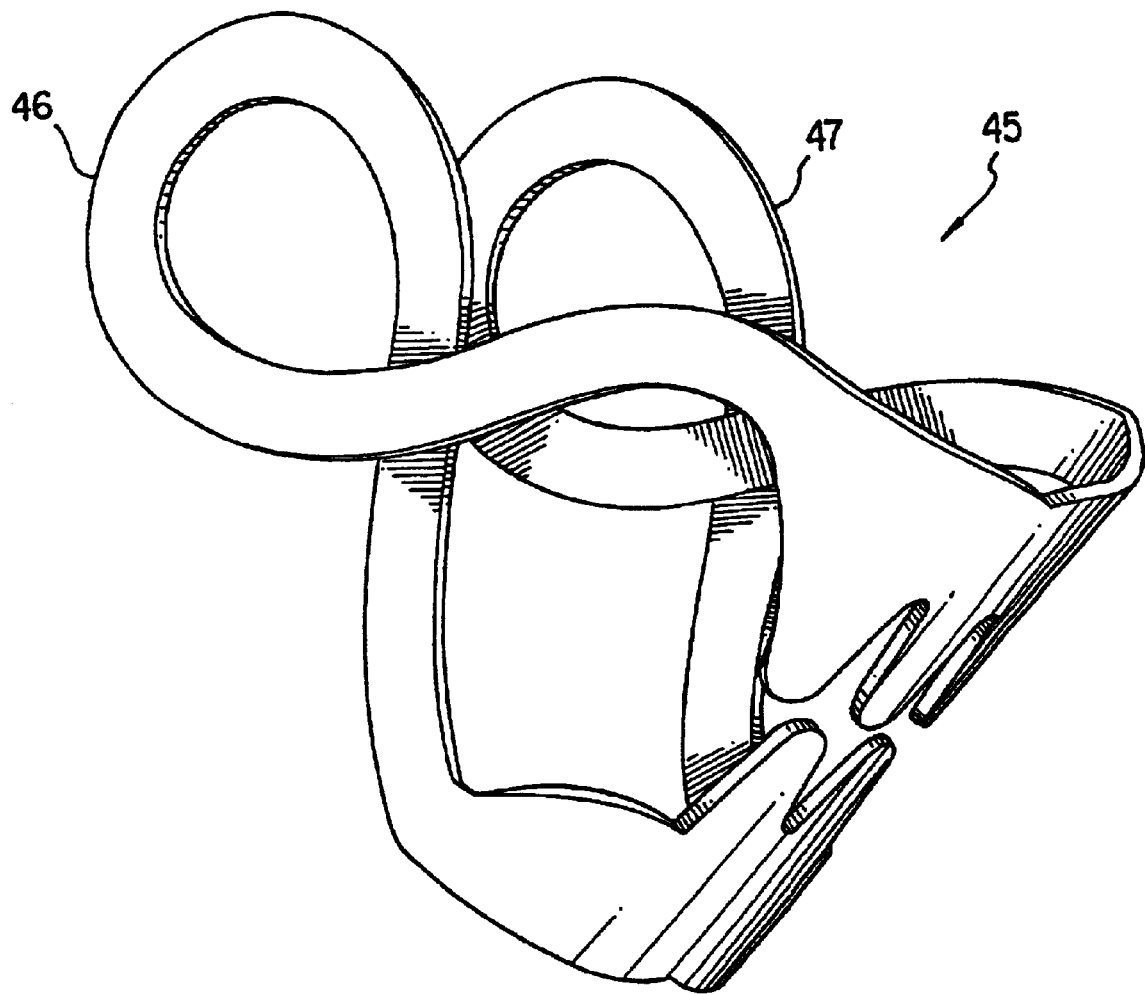
FIG. 22 illustrates a seventh embodiment for the surgical clip which includes a torsion design for the first and second joints.

FIG. 22 illustrates a seventh embodiment of a surgical clip 45 that includes a torsion design for first joint 46 and second joint 47. The torsion design of the joints comprises a figure-eight configuration. Designing the joints in this configuration could be advantageous in that they could provide a high force potential when utilizing lower yield materials for the joints.

Figure 23:
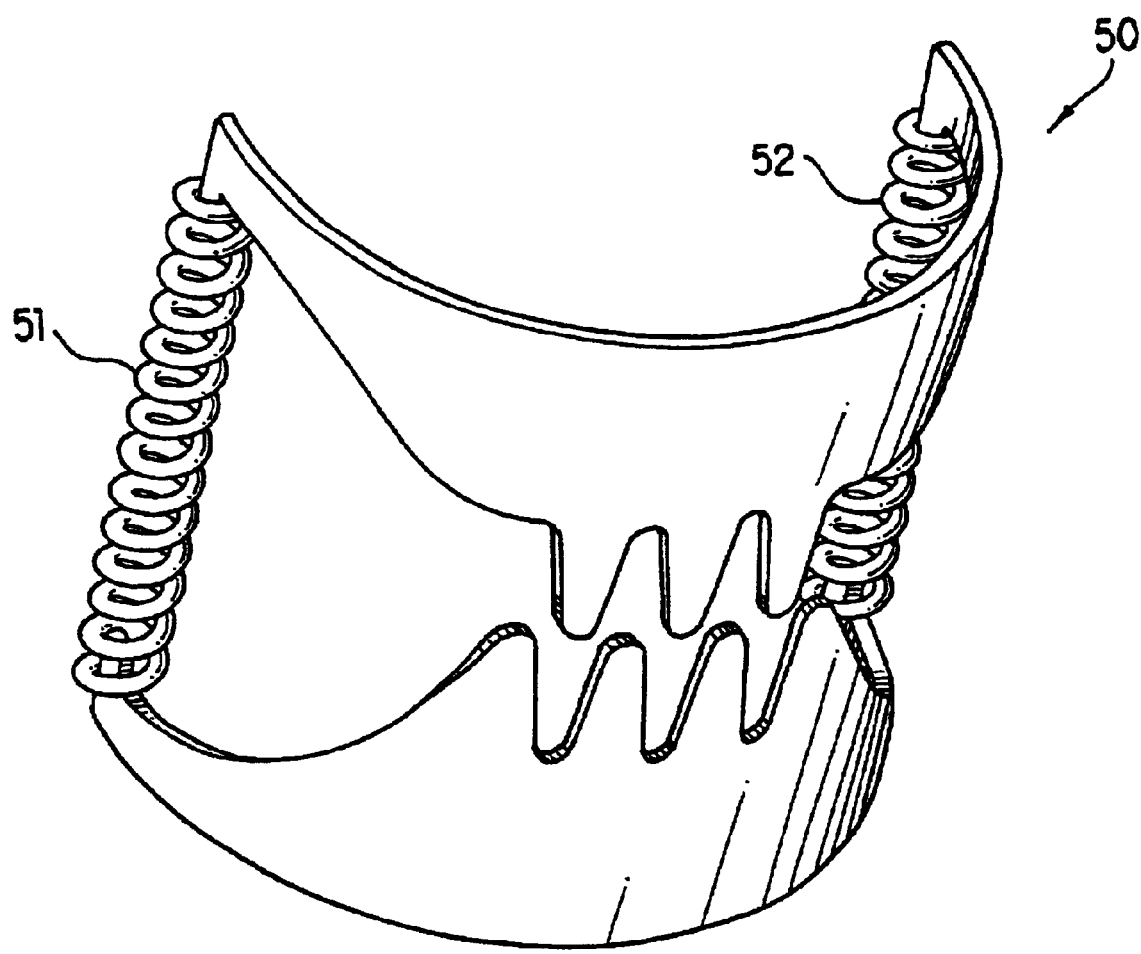
FIG. 23 illustrates an eighth embodiment for the surgical clip which utilizes compression springs as the joints.

FIGS. 23 through 31 illustrate alternative embodiments for the joints which utilize multiple and/or different components for the joints. As can be seen in FIG. 23, an eighth embodiment for surgical clip 50 is illustrated that utilizes compression springs for first joint 51 and second joint 52. The compression springs connect to the ends of the grasping surfaces and provide the biasing force to bias the grasping surfaces toward each other in their tissue grasping position.

Figure 24:
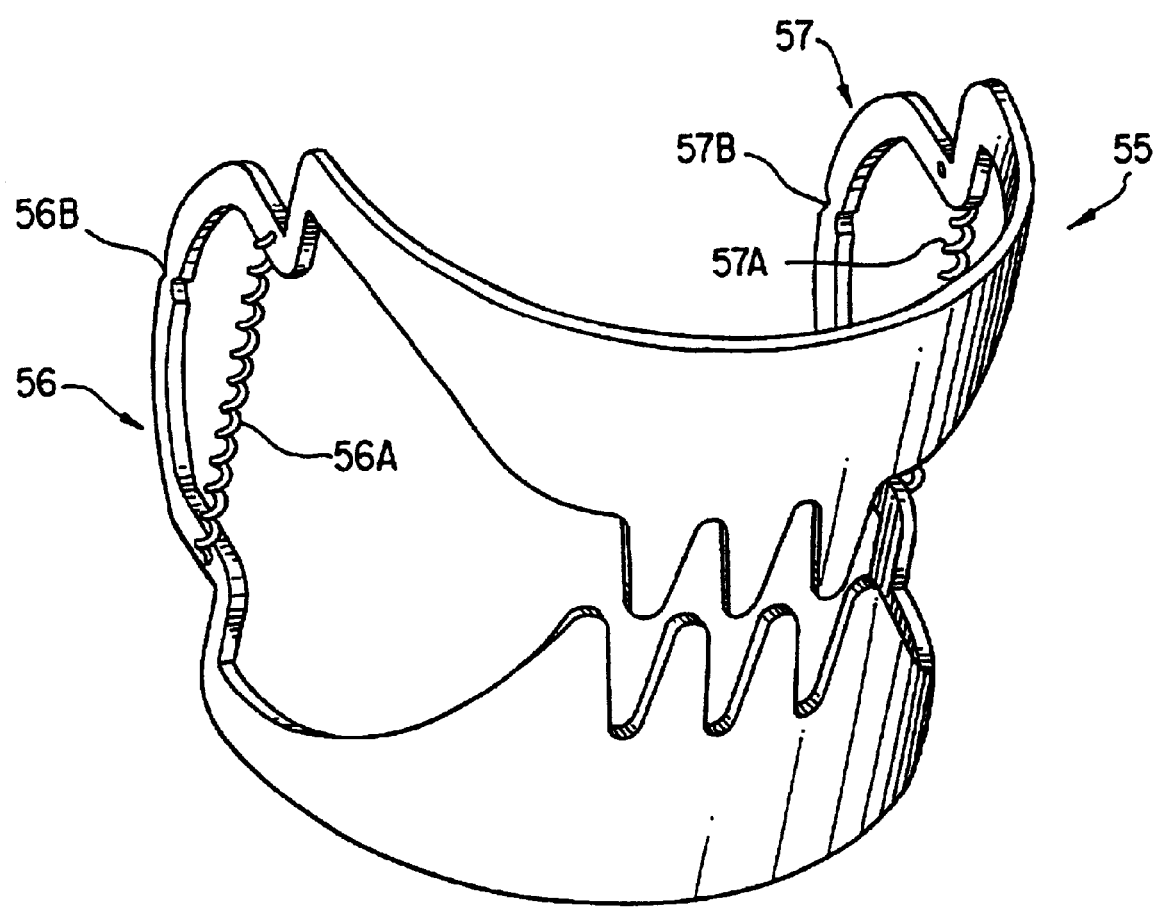
FIG. 24 illustrates a ninth embodiment for the surgical clip which utilizes a spring as a component of the joints.
Figure 25:
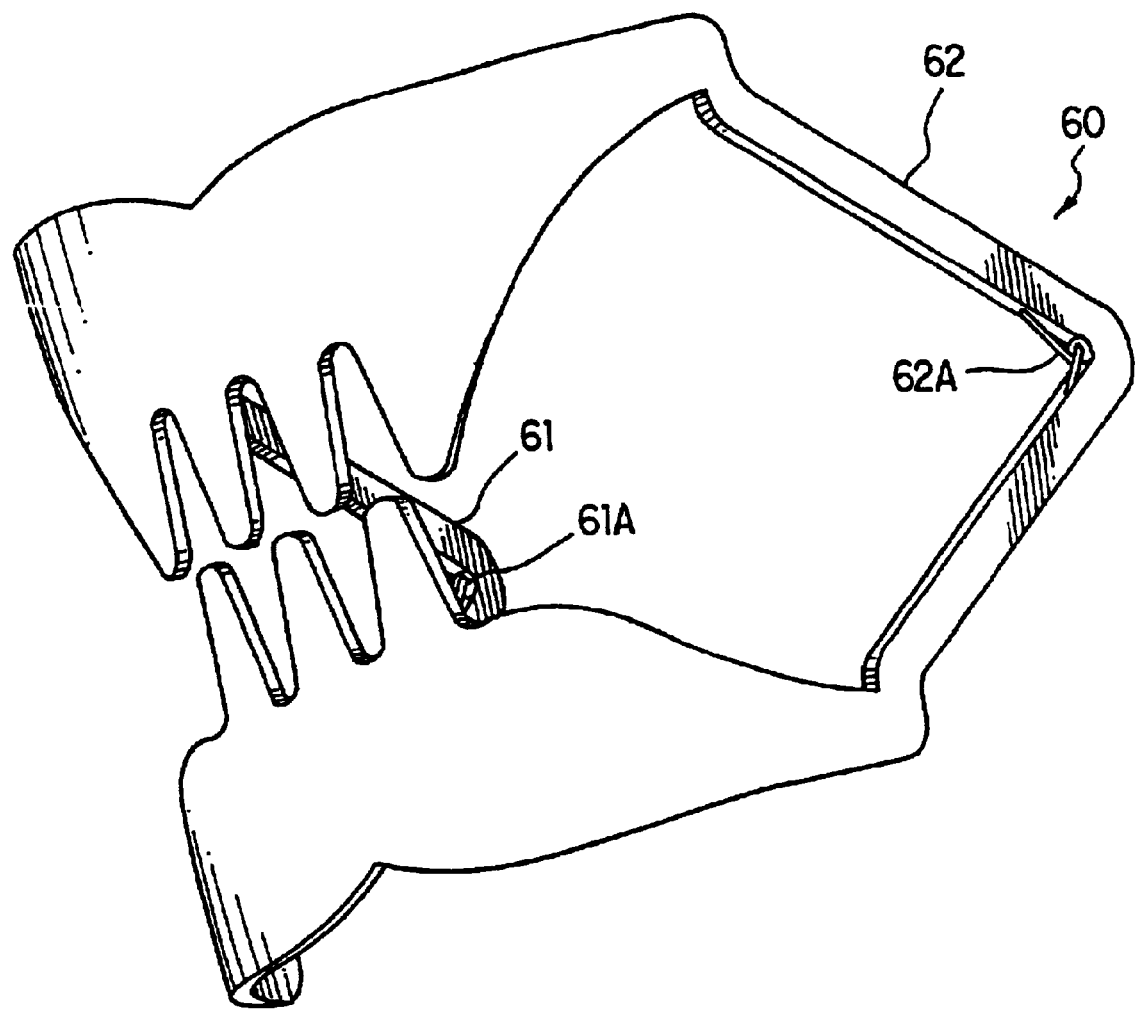
FIG. 25 illustrates a tenth embodiment for the surgical clip which utilizes a torsion spring as a component of the joints.
Figure 26:
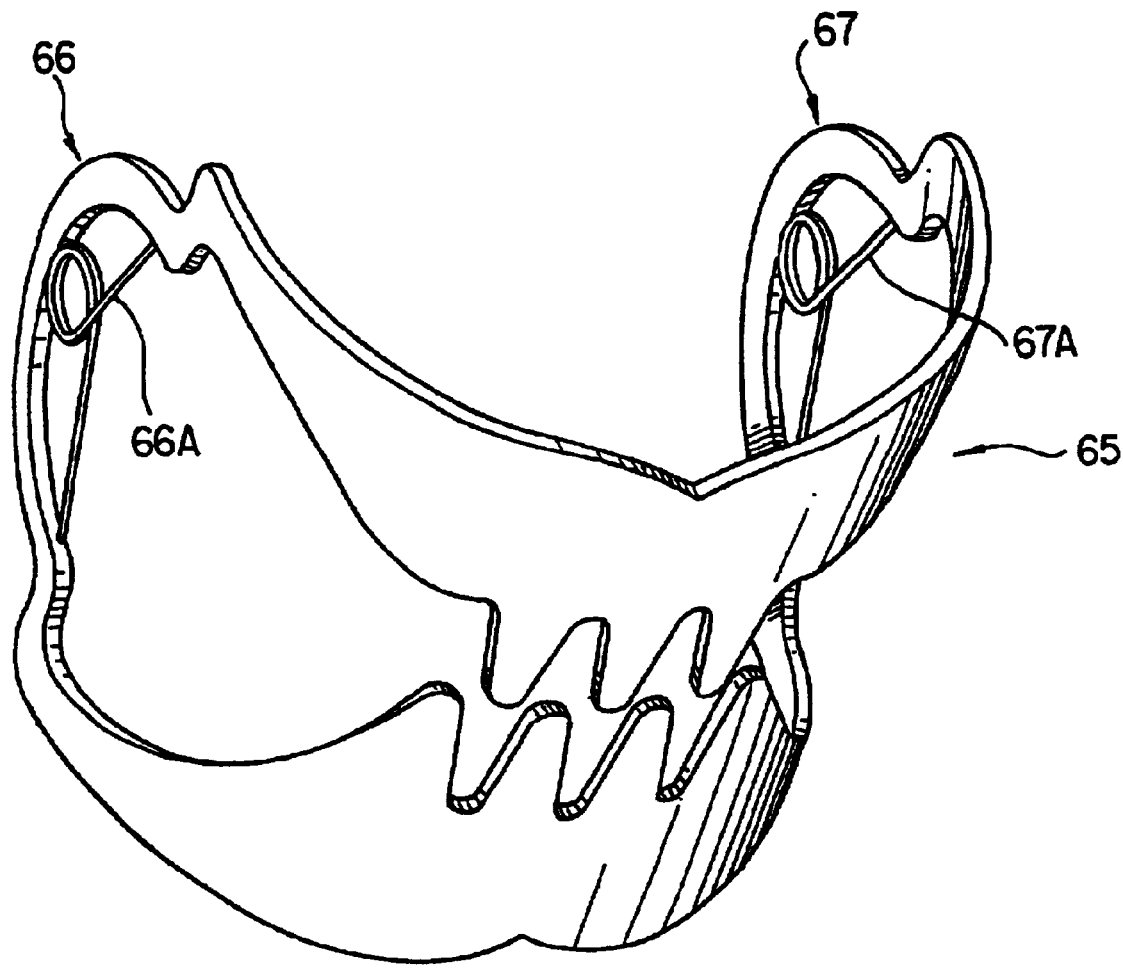
FIG. 26 illustrates an eleventh embodiment for the surgical clip which also utilizes a torsion spring as a component of the joints.

FIGS. 24 through 26 illustrate alternative embodiments for the joints where springs are used as an additional component in comprising a joint assembly. As can be seen in FIG. 24, a ninth embodiment for a surgical clip 55 includes a first extension spring 56A and a second extension spring 57A that are a component of the joint assemblies. Thus, the extension springs 56A, 57A may be utilized to assist the joints 56 and 57, respectively, in applying the biasing force to the first and second grasping surfaces. As is also illustrated in FIG. 24, hinge point 56B of joint 56 may be notched as shown so that the majority of the force that is applied is controlled by the springs. Similarly, second joint 57 is notched at its hinge point 57B. Alternatively, the hinge points may be formed as pinned pivot points so that the springs provide the entire closing force on the tissue grasping surfaces.

FIG. 25 illustrates a tenth embodiment for a surgical clip 60 that includes torsion springs 61A and 62A as components of first joint 61 and second joint 62, respectively. Similar to the springs of FIG. 24, torsion spring 61A and 62A may be utilized to assist in providing a closing force to the tissue grasping surfaces. The force applied by the torsion springs is a force in addition to the force applied by the base material of the first and second joints. Alternatively, the joints may also include a pinned pivot joint as described above so that the torsion springs provide the entire closing force.

Similarly, FIG. 26 illustrates an eleventh embodiment for a surgical clip 65 that has a first joint 66 that includes a torsion spring 66A and a second joint 67 that includes a second torsion spring 67A. The torsion springs 66A and 67A function as described in the previous embodiments.

Figure 27:
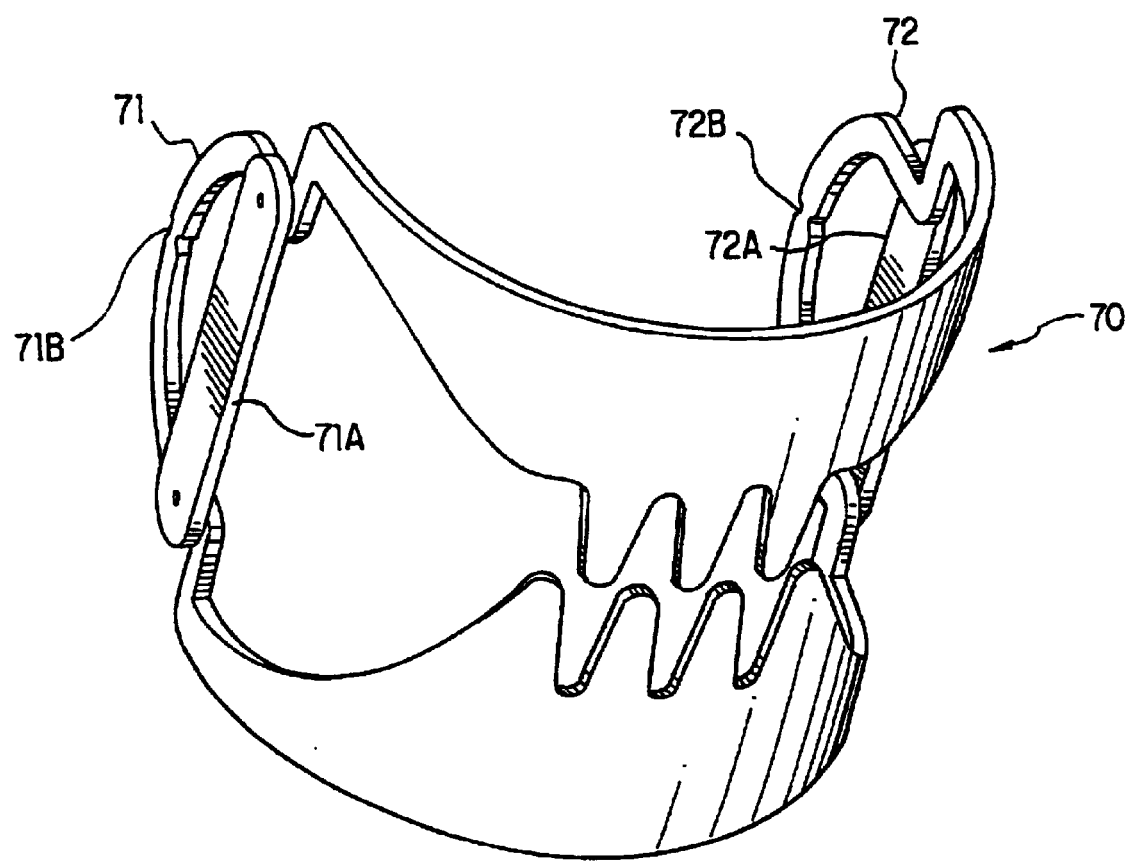
FIG. 27 illustrates a twelfth embodiment for the surgical clip which utilizes an elastomeric band as a component of the joints.

FIGS. 27 through 31 illustrate alternative embodiments for the surgical clip which include elastomeric bands as components of the joints. As can be seen in FIG. 27, a twelfth embodiment for a surgical clip 70 is illustrated that has a first joint 71 and a second joint 72. Elastomeric band 71A is included as a component of first joint 71 and elastomeric band 72A is included as a component of second joint 72. As can be seen in FIG. 27, the elastomeric bands 71A and 72A are formed such that they are able to stretch, and thus elongate, when the tissue grasping portions are moved to their tissue receiving position and thus assist their respective joints in applying the biasing force to the grasping portions to return them to their tissue grasping position. In this embodiment for surgical clip 70, the elastomeric bands 71A and 72A are attached at first joint 71 and second joint 72, respectively, such as by utilizing an attachment mechanism, e.g., a pin or a screw. The elastomeric bands are attached at an outer surface of their respective joints. As can be further seen in FIG. 27, first joint 71 includes a notch 71B at its pivot point and second joint 72 includes a notch 72B at its pivot point.

Figure 28:
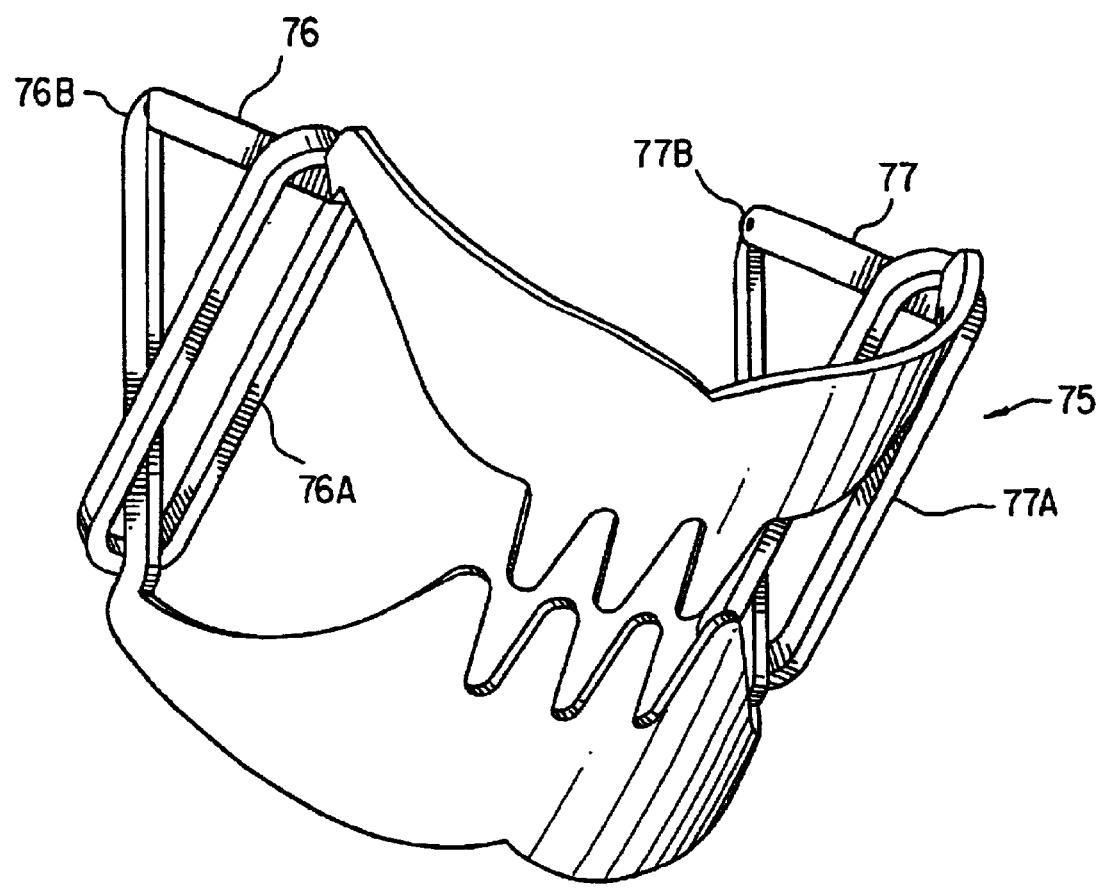
FIG. 28 illustrates a thirteenth embodiment for the surgical clip which utilizes an elastomeric band as a component of the joints.

FIG. 28 illustrates a thirteenth embodiment for a surgical clip 75 that includes elastomeric bands 76A and 77A as parts of first joint 76 and second joint 77, respectively. In contrast to the embodiment of FIG. 27, the embodiment of FIG. 28 includes oval-shaped elastomeric bands that are positioned on and around their respective joints rather than being attached to an outside surface of the joints. Additionally, in the embodiment of FIG. 28, first joint 76 includes a pinned pivot point 76B and second joint 77 includes a pinned pivot point 77B such that the entire biasing force which biases the first grasping surface toward the second grasping surface is provided solely by the elastomeric bands.

Figure 29:
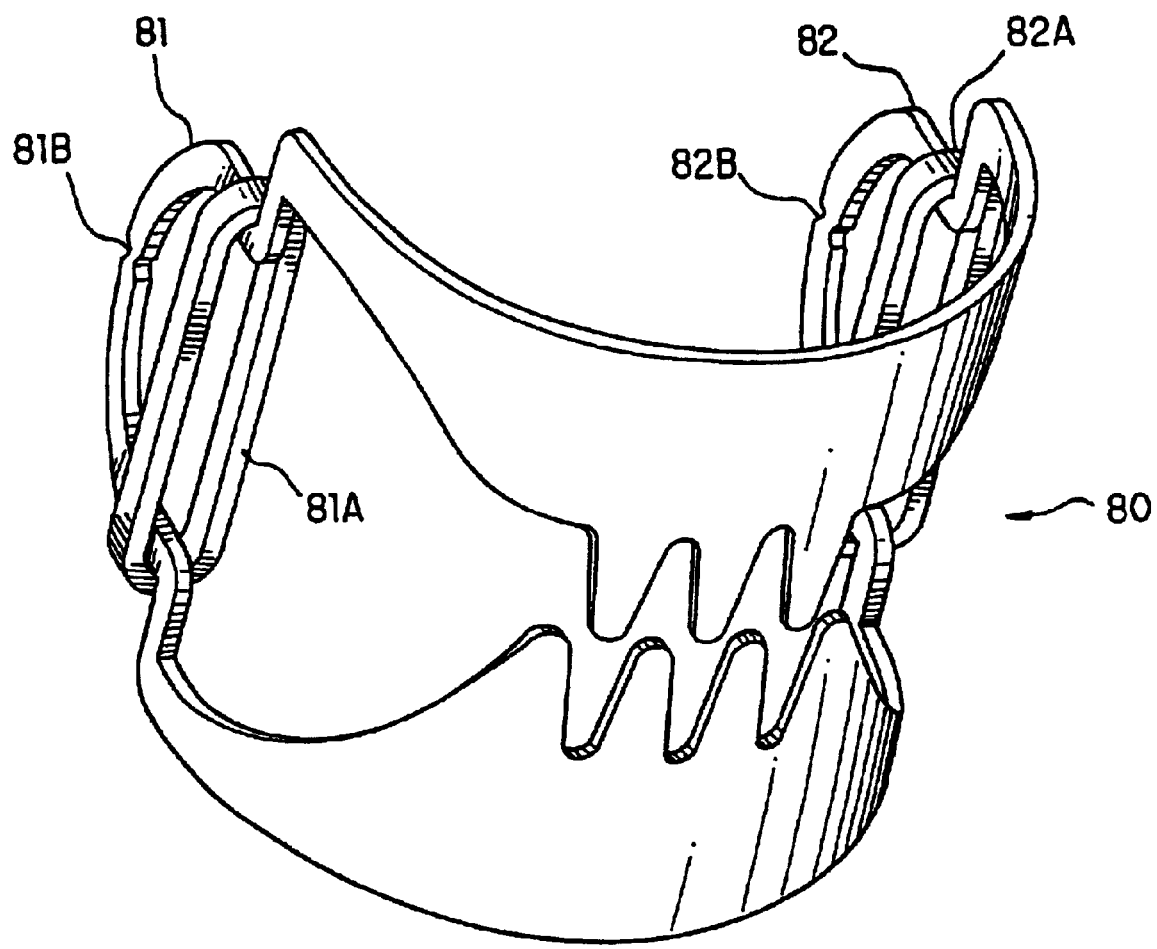
FIG. 29 illustrates a fourteenth embodiment for the surgical clip which utilizes an elastomeric band as a component of the joints.

FIG. 29 illustrates a fourteenth embodiment for a surgical clip 80 that also includes an elastomeric band 81A as a component of first joint 81 and an elastomeric band 82A as a component of second joint 82. The elastomeric bands of FIG. 29 are positioned on their respective joints similar to the manner that the elastomeric bands were positioned in the embodiment of FIG. 28 in that they are oval-shaped members and are disposed around, and on, their respective joints. However, in the embodiment of FIG. 29 as opposed to the embodiment of FIG. 28, first joint 81 includes a notched pivot point 81B and second joint 82 includes a notched pivot point 82B such that the elastomeric bands assist in providing the biasing force to the first and second grasping surfaces and thus do not apply the full biasing force. The base material of the first and second joints also provide a biasing force to the first and second grasping surfaces.

Figure 30:
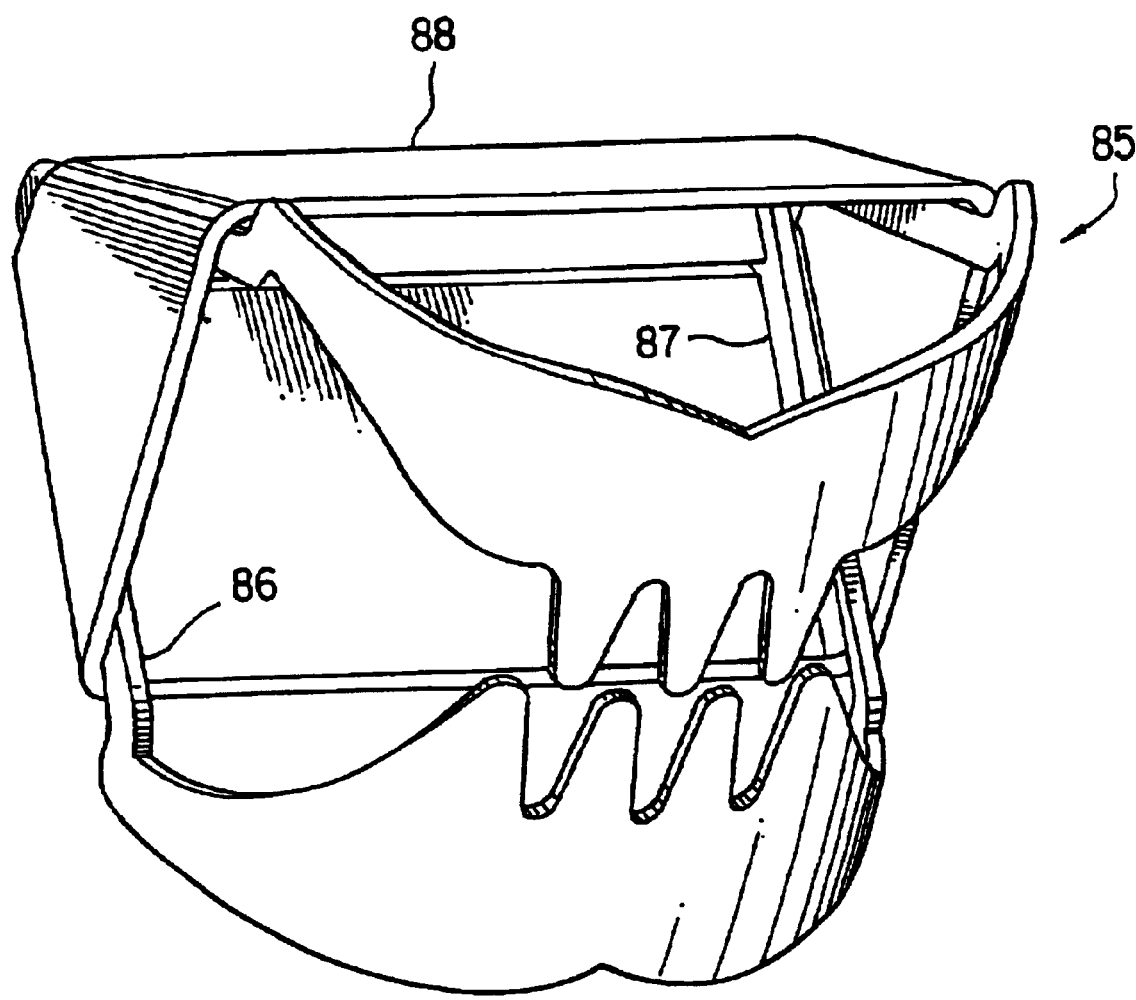
FIG. 30 illustrates a fifteenth embodiment for the surgical clip which utilizes an elastomeric band as a component of the joints.

FIG. 30 illustrates a fifteenth embodiment for a surgical clip 85 in accordance with the principles of the present invention. Surgical clip 85 also has a first joint 86 and a second joint 87 and includes a single elastomeric band 88 which is disposed over and around both joints 86 and 87.

Thus, in contrast to the previously disclosed embodiments where two elastomeric bands were utilized, one for each joint of the surgical clip, the embodiment of FIG. 30 utilizes a single elastomeric band 88 that can either assist in providing a biasing force to the first and second grasping portions or can provide the entire biasing force to the first and second grasping surfaces.

Figure 31:
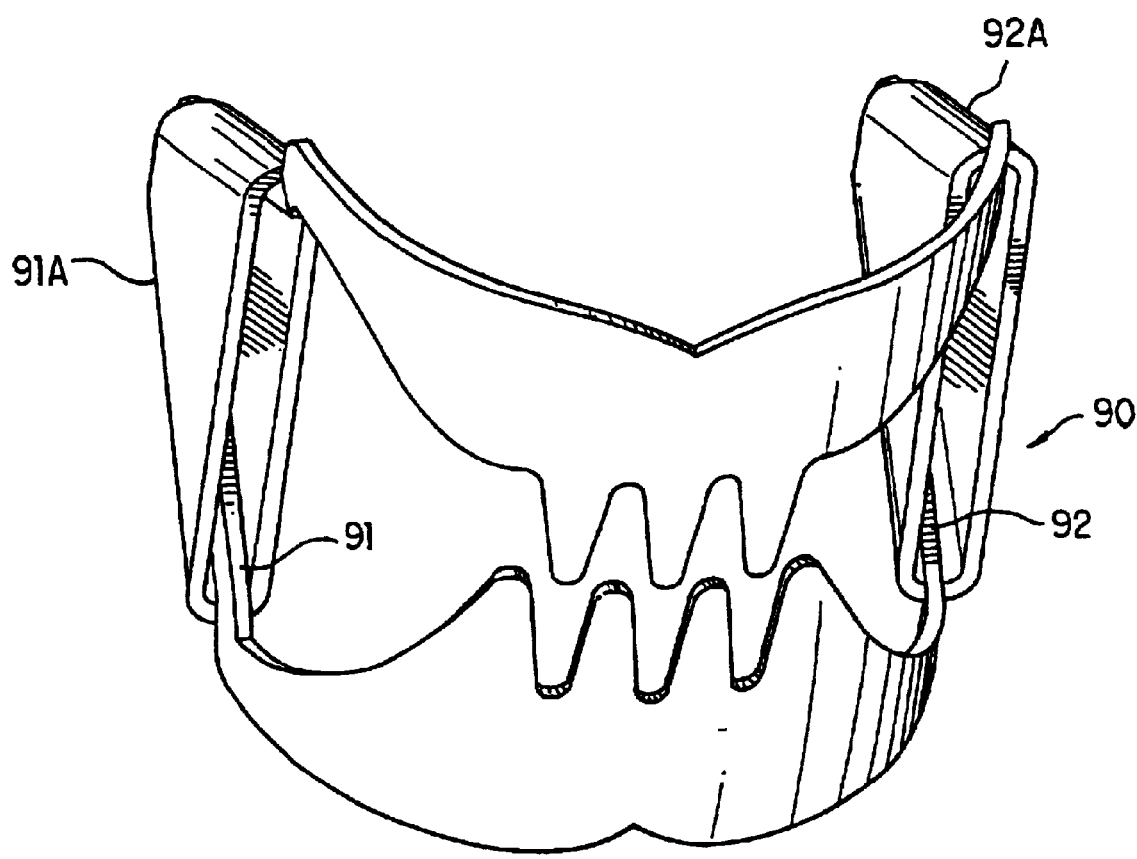
FIG. 31 illustrates a sixteenth embodiment for the surgical clip which utilizes an elastomeric band as a component of the joints.

FIG. 31 illustrates a sixteenth embodiment for a surgical clip 90. Again, surgical clip 90 has a first joint 91 and a second joint 92 and included in each joint is an elastomeric band 91A and 92A, respectively. Elastomeric bands 91A and 92A may either assist in providing the biasing force to the first and second grasping surfaces or may provide the entire biasing force to the grasping surfaces. However, in contrast to the embodiments of FIGS. 28 and 29, the embodiment of FIG. 31 includes an elongated elastomeric band that is disposed on the entirety of its respective joint. Thus, the elastomeric band is formed in a generally triangularly-shaped configuration to conform to the shape of the joint on which it is disposed.

Figure 32:
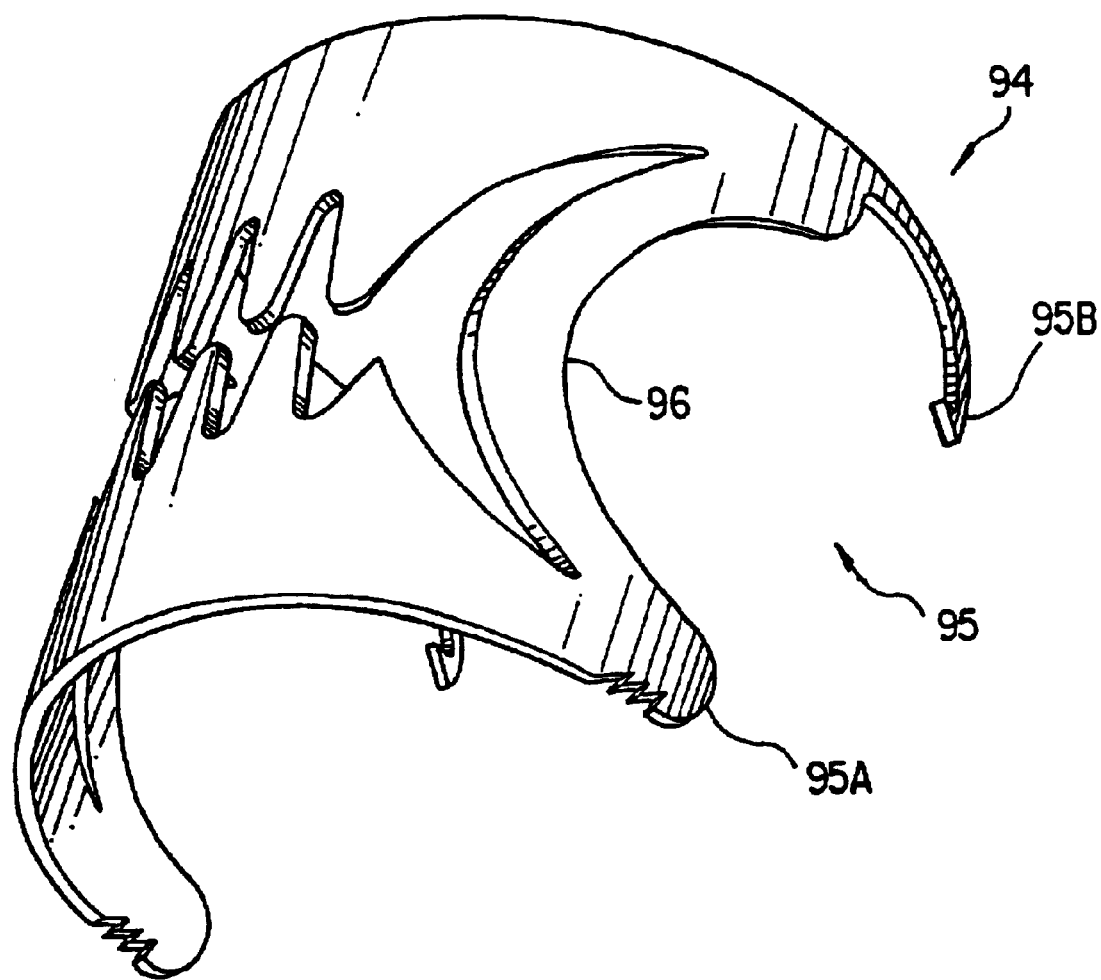
FIG. 32 illustrates a seventeenth embodiment for the surgical clip which includes a first embodiment for a lock to lock the first and second tissue grasping surfaces in the tissue receiving position.
Figure 33:
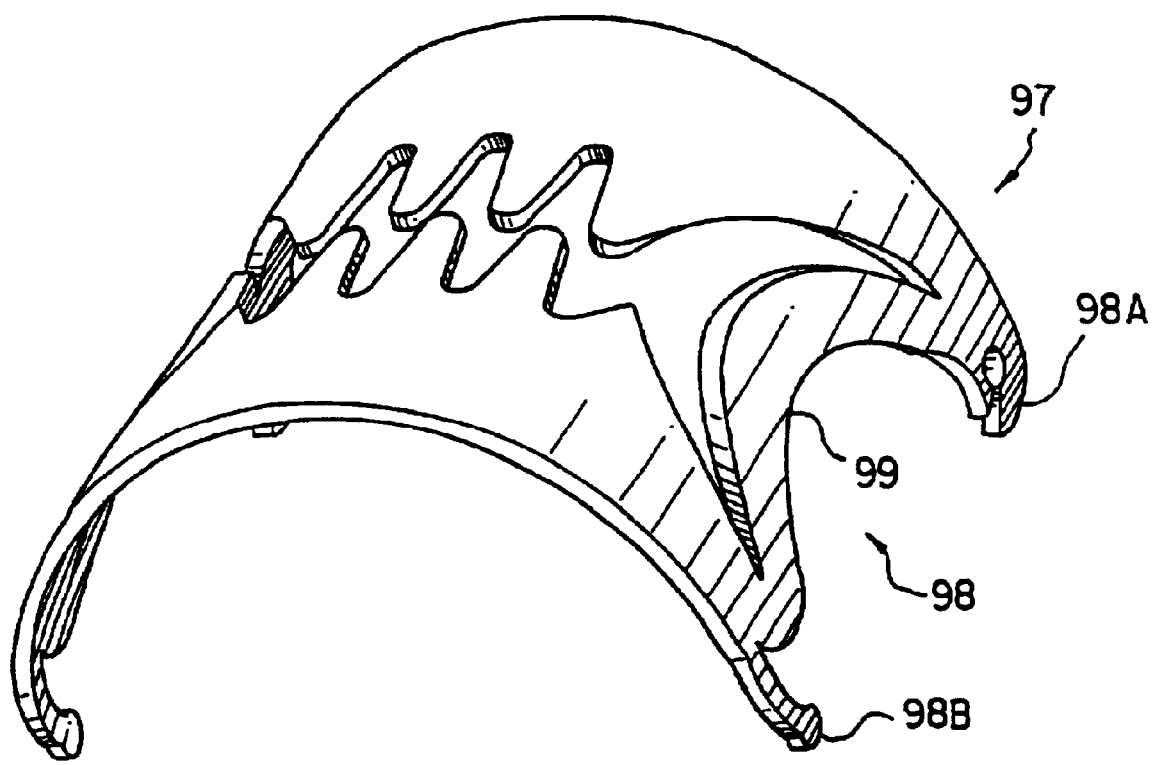
FIG. 33 illustrates an eighteenth embodiment for the surgical clip which includes a second embodiment for a lock to lock the first and second tissue grasping surfaces in the tissue receiving position.

As discussed previously, when the surgical clip is disposed on the endoscope cap in its tissue receiving position, the tissue grasping surfaces of the surgical clip may exert a force on the endoscope cap which may disadvantageously effect the deployment of the surgical clip off of the endoscope cap. Therefore, it may be desirable to provide a locking mechanism on the surgical clip that could assist in maintaining the surgical clip in its tissue receiving position and which could also serve to reduce the force applied by the surgical clip on the endoscope cap. However, once the surgical clip is deployed off of the endoscope cap, the lock would disengage under the biasing pressure applied by the connecting joints such that the tissue grasping surfaces of the surgical clip could return to their tissue grasping position. FIGS. 32 and 33 illustrate two possible alternatives for providing such a locking mechanism.

FIG. 32 illustrates a seventeenth embodiment for a surgical clip 94 that includes a first embodiment for a lock mechanism. Lock mechanism 95 includes a plurality of notches 95A at a first end of surgical clip 94 on a first side of surgical clip 94 and a pawl 95B on a second end of surgical clip 94 on the first side of surgical clip 94. When surgical clip 94 is positioned in its tissue receiving position, pawl 95B is received within one of the plurality of notches 95A to assist in locking surgical clip 94 in its tissue receiving position until it is deployed off of the endoscope cap. As discussed previously, when the surgical clip 94 is deployed off of the endoscope cap, the biasing force applied by joint 96 to return the grasping surfaces to their tissue grasping position is sufficient to overcome the engagement force between pawl 95B and notches 95A such that pawl 95B will become disengaged from one of the notches 95A such that surgical clip 94 may return to its tissue grasping position. As can be seen in FIG. 32, a second side of surgical clip 94 also includes a pawl and notch locking mechanism.

As can be seen in FIG. 33, an eighteenth embodiment for a surgical clip 97 is illustrated which includes a second embodiment for a lock 98. Lock 98 operates similarly to the lock as described in FIG. 32, however, the interlocking mechanism now utilizes a ball joint 98B that is received within a slot 98A that is defined on a side in an end of surgical clip 97. Again, lock 98 serves to assist in retaining surgical clip 97 in its tissue receiving position and becomes disengaged after surgical clip 97 is deployed from the endoscope cap and joint 99 biases the grasping surfaces toward each other to their tissue grasping position. Again, a second side of surgical clip 97 may also include a lock 98.

Other alternative designs are contemplated for assisting in deploying the surgical clip off of the endoscope cap. For example, the endoscope cap could include a surface that is conducive to minimizing the frictional forces between the surgical clip and the endoscope cap. This surface could be comprised of hard, smooth surfaces which could include any of a variety of surface treatments to minimize the frictional forces between the surgical clip and the endoscope cap.

Alternatively, it is contemplated that another mechanism that could be utilized to reduce the clamping force as applied by the surgical clip on the endoscope cap is a cam-type hinge. The cam-type hinge would reduce the closing force applied by the surgical clip on the endoscope cap when the surgical clip is in its tissue receiving position. Upon deployment of the surgical clip, the full closing force of the surgical clip would be employed. This cam-type hinge is similar in design and concept to a that used in a compound archery bow.

The present invention may be utilized for any of a variety of different applications and surgical procedures. Whereas the present invention may be utilized in endoscopic techniques for clipping bleeding, or potentially bleeding, peptic ulcers, either gastric or duodenal, other uses of the present invention are contemplated. For example, the present invention can be utilized for all hemorrhaging, or potentially hemorrhaging, gastrointestinal lesions. These include all of the indications presently known for the traditional treatments. A partial list includes:

Esophageal Varices and ulcers
Mallory-Weiss Tears
Gastric erosions
Esophagitis
Erosive Duodenitis
Tumors
Angiodysplasia
Bleeding polyp stalks
Diverticular Bleeding Other endoscopic indications could be developed for clinically induced wounds. A representative list which is not intended to be all inclusive includes:

Laparoscopic repair of Gall Bladder perforation during Cholecystectomy
Repair of perforations to biopsy or mucosectomy
Repair of excessive bleeding due to biopsy or mucosectomy
Repair of incomplete resections
Closing of induced wounds to gain access through GI lumens into other anatomical areas like the outside of the gall bladder, liver, and pancreas
Colonic perforation related to colonoscopy There are also vascular applications for the surgical clip and delivery system. Miniaturization of the surgical clip and the delivery system could permit vascular repair. Visualization could be either direct, radiograph, MRI or sonic. The applications are for minimally invasive surgery, aneurysm repair and graph/implant attachment.

Again, as discussed above, the present invention could be utilized for any of a variety of procedures, including to close an organ perforation from inside a lumen by approximating and compressing the wound edges of the perforated tissue.

The disclosed embodiments are illustrative of the various ways in which the present invention may be practiced. Other embodiments can be implemented by those skilled in the art without departing from the spirit and scope of the present invention.

What is claimed is:

1. A system for delivering a surgical clip to a surgical site within a patient's body to compress body tissue, comprising:
    an endoscopic device;
    an endoscope cap disposed on a distal end of said endoscopic device;
    a surgical clip removably disposed on an outside surface of said endoscope cap and having a potential energy transformable into energy for grasping tissue when said surgical clip is deployed; and
    a deployment device associated with said surgical clip.
2. The system of claim 1 further comprising a tissue grasping device disposed through said endoscopic device.
3. The system of claim 1 wherein said outside surface of said endoscopic cap is treated to reduce a frictional force between said outside surface and said surgical clip.
4. The system of claim 2 wherein said tissue grasping device comprises at least one spring-formed J-shaped barb.
5. The system of claim 1 wherein said deployment device comprises a cable attached at a first end to said surgical clip.
6. The system of claim 1 wherein said deployment device comprises a tubular member disposed around said endoscopic device and adapted to deploy said surgical clip.
7. The system of claim 1 wherein said deployment device comprises a balloon disposed between said endoscope cap and said surgical clip.
8. The system of claim 1 further comprising a balloon disposed between said endoscope cap and said surgical clip and wherein a portion of said balloon proximal to said surgical clip impels a distal motion of said surgical clip with respect to said endoscope cap.
9. The system of claim 1 further comprising a foam member disposed on said endoscope cap, a portion of said foam member which is located proximal to said surgical clip deploys said surgical clip.
10. The system of claim 1 wherein said surgical clip is in a martensite phase when said surgical clip is disposed on said outside surface of said endoscope cap.
11. The system of claim 10 further comprising a heating element associated with said surgical clip.
12. The system of claim 1 wherein said surgical clip is in an austentite phase when said surgical clip is disposed on said outside surface of said endoscope cap.
13. The system of claim 1 when said surgical clip is comprised of a shape-memory alloy.
14. The system of claim 1 when said surgical clip is comprise of a shape-memory polymer.
15. The system of claim 1 when said surgical clip is comprised of a shape-memory composite.
16. The system of claim 1 when said surgical clip is comprised of spring steel.
17. The system of claim 1 when said surgical clip is comprised of titanium.
18. The system of claim 1 when said surgical clip is comprised of a high-yield polymer.
19. The system of claim 1 wherein a plurality of surgical clips is disposed on said outside surface of said endoscope cap.
20. The system of claim 1 wherein said surgical clip comprises a plurality of grasping surfaces suitable for penetrating a submucosa of the body tissue.
21. The system of claim 20 wherein said grasping surfaces are connected by a plurality of joints.
22. The system of claim 21 wherein said joints are formed in a figure eight configuration.
23. The system of claim 21 wherein each of said joints further comprises an extension spring.

24. The system of claim 21 wherein each of said joints further comprises a hinge point.

25. The system of claim 23 wherein the extension springs control a majority of the energy when the surgical clip is deployed.

26. The system of claim 24 wherein each hinge point is notched.

27. The system of claim 24 wherein each hinge point is formed as a pinned pivot point.

28. The system of claim 21 wherein each of said joints further comprises a torsion spring.

29. The system of claim 28 wherein each of said joints further comprises a pinned pivot point.

30. The system of claim 21 wherein said joints store the potential energy mechanically.

31. The system of claim 21 wherein said joints store the potential energy according to a material process.

32. The system of claim 1 wherein said deployment device comprises:
    a force generator disposed around said endoscopic device and including:
        an engagement member at least partially disposed within said force generator and movable between a first position where said engagement member does not deploy said surgical clip off of said endoscope cap and a second position where said engagement member deploys said surgical clip; and
        an actuator operably associated with said engagement member.

33. The system of claim 32 wherein said actuator is a compression spring.

34. The system of claim 33 further comprising a retention spring disposed around a portion of said engagement member and biasing said engagement member in said first position.

35. The system of claim 32 wherein said actuator is a pressurized chamber and wherein said force generator includes a first seal disposed between a piston included on said engagement member and an inside wall of said force generator and a second seal disposed between said piston and an outside wall of said force generator.

36. The system of claim 32 wherein said actuator is an electrical coil.

37. A method for delivering a surgical clip to a surgical site within a patient's body to compress body tissue, comprising the steps of:
    disposing a surgical clip on an outside surface of an endoscope cap such that the clip is in an austenite phase, said endoscope cap disposed on a distal end of an endoscopic device;
    deploying said endoscopic device to a site within the patient's body such that said surgical clip is positioned proximate to the body tissue to be compressed;
    drawing the body tissue within said endoscope cap; and
    deploying said surgical clip from said outside surface of said endoscope cap such that the tissue grasping surfaces move near one another.

38. The method of claim 37 wherein said step of drawing the body tissue within said endoscope cap comprises the step of applying a suction through said endoscopic device to said body tissue.

39. The method of claim 37 wherein said step of drawing the body tissue within said endoscope cap comprises the steps of:
    grasping the body tissue with a grasping device; and
    pulling the body tissue into said endoscope cap.

40. The method of claim 39 wherein said step of grasping the body tissue with a grasping device comprises the step of screwing a distal end of a threaded tool into the body tissue.

41. The method of claim 39 wherein said step of grasping the body tissue with a grasping device comprises the step of inserting at least one spring-formed, J-shaped barb into the body tissue.

42. The method of claim 37 wherein said step of deploying said surgical clip from said outside surface of said endoscope cap comprises the step of pulling a second end of a cable in a proximal direction wherein a first end of said cable is attached to said surgical clip.

43. The method of claim 37 wherein said step of deploying said surgical clip from said outside surface of said endoscope cap comprises the step of pushing a tubular member disposed around said endoscopic device to push said surgical clip off of said endoscope cap.

44. The method of claim 37 wherein said step of deploying said surgical clip from said outside surface of said endoscope cap comprises the step of inflating a balloon disposed between said endoscope cap and said surgical clip.

45. The method of claim 37 wherein said step of deploying said surgical clip comprises the step of actuating a deployment device disposed on said endoscope cap wherein when said deployment device is actuated a distal end of an engagement member extends from said deployment device to engage said surgical clip and push said surgical clip off of said endoscope cap.

46. The method of claim 45 wherein said step of actuating said deployment device comprises the step of releasing a compression spring.

47. The method of claim 45 wherein said step of actuating said deployment device comprises the step of pressurizing a chamber contained within said deployment device.

48. The method of claim 45 wherein said step of actuating said deployment device comprises the step of electrically moving said engagement member.

49. The method of claim 37 further comprising the step of partially inflating a balloon disposed between said endoscope cap and said surgical clip, said partially inflated balloon having a diameter at a portion of said balloon which is located proximal to said surgical clip which is greater than a diameter of said surgical clip.

50. The method of claim 37 further comprising the step of providing a foam member on said endoscope cap, said foam member having a diameter at a portion of said foam member which is located proximal to said surgical clip which is greater than a diameter of said surgical clip.

51. The method of claim 37 further comprising the steps of:
    providing a cover over said surgical clip prior to the step of deploying the endoscopic device to the site within the patient's body; and
    retracting said cover from covering said surgical clip prior to the step of deploying said surgical clip from said outside surface of said endoscope cap.

52. The method of claim 51 wherein said cover is an intubation overtube.

53. The of method claim 37 wherein said surgical clip is in a martensite phase when said surgical clip is disposed on said outside surface of said endoscope cap and further including the step of heating said surgical clip to transform said surgical clip to an austenite phase after the step of deploying said surgical clip from said outside surface of said endoscope cap.

54. The method of claim 53 wherein said step of heating said surgical clip comprises the step of supplying heated water to said surgical clip through a working channel of said endoscopic device.

55. A surgical clip, the surgical clip deliverable at a site within a patient's body by an endoscopic device, comprising:
- a plurality of grasping surfaces;
- a plurality of joints connecting each one of said plurality of grasping surfaces; and
- wherein said grasping surfaces are movable between a tissue receiving position and a tissue grasping position and wherein when said grasping surfaces are in said tissue receiving position said grasping surfaces are adapted to be received on an outer surface of the endoscopic device.

56. A surgical clip according to claim 55 wherein when said grasping surfaces are in said tissue receiving position said surgical clip stores an energy potential to force said grasping surfaces into said tissue grasping position.

57. The surgical clip of claim 55 wherein when said first and second tissue grasping surfaces are in said tissue grasping position said first and second joints bias said first tissue grasping surface toward said second tissue grasping surface and wherein when said first and second tissue grasping surfaces are moved to said tissue receiving position by a force, said first and second joints store an energy potential within them, said energy potential returning said first grasping surface and said second grasping surface to said tissue grasping position upon removal of said force.

58. The surgical clip of claim 55 wherein said first and second joints are formed integrally with said first and second tissue grasping surfaces.

59. The surgical clip of claim 55 wherein each of said first and second joints include a semi-circular portion included between said respective first and second ends of said joints, said semi-circular portion extending toward said first and second elongated tissue grasping surfaces and wherein when said first and second joints are in said tissue receiving position said first end of each of said first and second joints contacts said respective second end of each of said first and second joints.

60. The surgical clip of claim 55 wherein each of said first and second joints includes a compression spring disposed between said first end and said second end of said respective joint.

61. The surgical clip of claim 55 wherein each of said first and second joints includes a torsion spring disposed between said first end and said second end of said respective joint.

62. The surgical clip of claim 55 wherein each of said first and second joints include an elastomeric band disposed between said first end and said second end of said respective joint.

63. The surgical clip of claim 55 further comprising a lock on a first side of said surgical clip.

64. The surgical clip of claim 63, said lock including a pawl and a notch, said pawl releasably engageable with said notch.

65. The surgical clip of claim 63, said including a slot defined by said first side of said surgical clip and a ball joint, said ball joint receivable within said slot.

66. The surgical clip of claim 55 wherein each of said first and second joints include a cam-type hinge.

\* \* \* \* \*